US009707127B2

(12) United States Patent
Kadziauskas et al.

(10) Patent No.: US 9,707,127 B2
(45) Date of Patent: *Jul. 18, 2017

(54) MODULATED PULSED ULTRASONIC POWER DELIVERY SYSTEM AND METHOD

(71) Applicant: Abbott Medical Optics Inc., Santa Ana, CA (US)

(72) Inventors: Kenneth E. Kadziauskas, Coto de Caza, CA (US); Paul W. Rockley, Corona Del Mar, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/503,827

(22) Filed: Oct. 1, 2014

(65) Prior Publication Data

US 2015/0202080 A1 Jul. 23, 2015

Related U.S. Application Data

(60) Division of application No. 13/200,061, filed on Sep. 16, 2011, now Pat. No. 8,852,138, which is a division (Continued)

(51) Int. Cl.
*A61B 19/00* (2006.01)
*A61F 9/007* (2006.01)
(Continued)

(52) U.S. Cl.
CPC .......... *A61F 9/00745* (2013.01); *B06B 1/023* (2013.01); *B06B 1/0215* (2013.01);
(Continued)

(58) Field of Classification Search
CPC .. A61F 9/007; A61F 9/00736; A61F 9/00745; A61F 9/00754; A61F 9/008;
(Continued)

(56) References Cited

U.S. PATENT DOCUMENTS 2,434,480 A 1/1948 Anderson
3,857,387 A 12/1974 Shock
(Continued)

FOREIGN PATENT DOCUMENTS

CA 2242328 A1 5/1998
DE 19940712 A1 3/2001
(Continued)

OTHER PUBLICATIONS

Davis P.L., et al., "Cavitating Microbubbles Create Shock Waves that Emulsify Cataract," in: The Art of Phacoemulsification, Mehta K.R., et al., eds., Jaypee Brothers,New Delhi, 2001, pp. 45-50.
(Continued)

*Primary Examiner* — Ahmed Farah
(74) *Attorney, Agent, or Firm* — Abbott Medical Optics Inc.

(57) ABSTRACT

A method and apparatus for delivering energy during a surgical procedure such as phacoemulsification is provided. The method and apparatus include applying energy during at least one pulsed energy on period, typically sufficient or intended to rapidly induce and beneficially employ transient cavitation. Applying energy during the pulsed energy on period comprises applying energy during a first high energy period, and applying energy during a second nonzero lower energy period.

8 Claims, 24 Drawing Sheets

Related U.S. Application Data of application No. 12/005,865, filed on Dec. 28, 2007, now Pat. No. 8,020,565, which is a continuation of application No. 10/387,335, filed on Mar. 12, 2003, now Pat. No. 7,316,664, which is a continuation-in-part of application No. 10/278,775, filed on Oct. 21, 2002, now Pat. No. 7,077,820.

(51) Int. Cl.
  *B06B 1/02* (2006.01)
  *G06F 12/02* (2006.01)
  *B06B 1/06* (2006.01)
  *A61B 17/00* (2006.01)
  *A61B 18/00* (2006.01)

(52) U.S. Cl.
  CPC ........... *B06B 1/0253* (2013.01); *B06B 1/06* (2013.01); *G06F 12/0223* (2013.01); *A61B 2017/00176* (2013.01); *A61B 2017/00194* (2013.01); *A61B 2018/00666* (2013.01); *B06B 2201/76* (2013.01); *Y02B 60/1225* (2013.01)

(58) Field of Classification Search
  CPC ........... A61F 9/00802; A61F 9/00804; A61F 2009/0087; A61N 7/00; A61N 2007/0039; A61N 2007/0043
  USPC ............ 604/19–22, 28; 606/4–6, 10–12; 600/437, 439; 601/2; 128/898
  See application file for complete search history.

(56) References Cited

U.S. PATENT DOCUMENTS

| | | |
|---|---|---|
| 3,885,569 A | 5/1975 | Judson |
| 3,941,122 A | 3/1976 | Jones |
| 4,184,510 A | 1/1980 | Murry et al. |
| 4,199,246 A | 4/1980 | Muggli |
| 4,343,111 A | 8/1982 | Inoue |
| 4,469,098 A | 9/1984 | Davi |
| 4,736,130 A | 4/1988 | Puskas |
| 4,808,948 A | 2/1989 | Patel et al. |
| 4,827,911 A * | 5/1989 | Broadwin ........ A61B 17/22012 310/17 |
| 4,903,696 A | 2/1990 | Stasz et al. |
| 4,952,834 A | 8/1990 | Okada |
| 4,954,960 A | 9/1990 | Lo et al. |
| 4,970,656 A | 11/1990 | Lo et al. |
| 4,983,901 A | 1/1991 | Lehmer |
| 5,001,649 A | 3/1991 | Lo et al. |
| 5,091,656 A | 2/1992 | Gahn |
| 5,209,221 A * | 5/1993 | Riedlinger ....... A61B 17/22004 601/2 |
| 5,213,569 A * | 5/1993 | Davis ................ A61F 9/00745 604/22 |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams et al. |
| 5,417,246 A | 5/1995 | Perkins et al. |
| 5,431,664 A | 7/1995 | Ureche et al. |
| 5,453,087 A | 9/1995 | Malinowski |
| 5,520,633 A | 5/1996 | Costin |
| 5,523,058 A | 6/1996 | Umemura et al. |
| 5,534,741 A | 7/1996 | Smith |
| 5,547,459 A | 8/1996 | Kaufman et al. |
| 5,549,632 A | 8/1996 | Lai |
| 5,582,578 A | 12/1996 | Zhong et al. |
| 5,591,127 A | 1/1997 | Barwick, Jr. et al. |
| 5,700,240 A | 12/1997 | Barwick, Jr. et al. |
| 5,733,256 A | 3/1998 | Costin |
| 5,738,677 A | 4/1998 | Colvard et al. |
| 5,766,146 A | 6/1998 | Barwick |
| 5,797,494 A | 8/1998 | Balling et al. |
| 5,800,365 A | 9/1998 | Zhong et al. |
| 5,808,396 A | 9/1998 | Boukhny |
| 5,836,959 A | 11/1998 | Seibel et al. |
| 5,852,794 A | 12/1998 | Staggs |
| 5,873,885 A | 2/1999 | Weidenbenner |
| 5,938,677 A | 8/1999 | Boukhny et al. |
| 5,971,980 A | 10/1999 | Sherman |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,027,515 A | 2/2000 | Cimino |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum et al. |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 * | 5/2002 | Cimino ............ A61B 17/32006 604/22 |
| 6,394,974 B1 | 5/2002 | Kadziauskas et al. |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,452,883 B2 | 9/2002 | Chan |
| 6,487,447 B1 | 11/2002 | Weimann et al. |
| 6,506,176 B1 | 1/2003 | Mittelstein et al. |
| 6,589,204 B1 | 7/2003 | Sussman et al. |
| 6,610,052 B2 | 8/2003 | Furumoto |
| 6,629,948 B2 | 10/2003 | Rockley et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 | 8/2004 | Kadziauskas et al. |
| 6,808,396 B2 | 10/2004 | Kawaguchi et al. |
| 6,884,252 B1 | 4/2005 | Urich et al. |
| 6,890,332 B2 * | 5/2005 | Truckai ............ A61B 17/22004 128/898 |
| 6,896,674 B1 | 5/2005 | Woloszko et al. |
| 6,908,472 B2 | 6/2005 | Wiener et al. |
| 6,939,317 B2 | 9/2005 | Zacharias |
| 6,962,583 B2 | 11/2005 | Kadziauskas et al. |
| 7,077,820 B1 | 7/2006 | Kadziauskas et al. |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 8,020,565 B2 | 9/2011 | Kadziauskas et al. |
| 8,202,287 B2 | 6/2012 | Staggs |
| 8,231,564 B2 | 7/2012 | Kadziauskas et al. |
| 8,887,735 B2 | 11/2014 | Kadzlauskas |
| 2001/0003155 A1 | 6/2001 | Rockley et al. |
| 2001/0003295 A1 | 6/2001 | Langlotz et al. |
| 2001/0003385 A1 | 6/2001 | Ise |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2002/0173814 A1 | 11/2002 | Jung et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2005/0054971 A1 | 3/2005 | Steen et al. |
| 2005/0209560 A1 | 9/2005 | Boukhny et al. |

(56) References Cited

U.S. PATENT DOCUMENTS

| | | |
|---|---|---|
| 2005/0209621 A1 | 9/2005 | Gordon et al. |
| 2005/0288665 A1 | 12/2005 | Woloszko |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0073214 A1 | 3/2007 | Dacquay et al. |
| 2007/0078379 A1 | 4/2007 | Boukhny et al. |
| 2008/0146989 A1 | 6/2008 | Zacharias |

FOREIGN PATENT DOCUMENTS

| | | |
|---|---|---|
| EP | 270819 A2 | 6/1988 |
| EP | 270819 A3 | 1/1989 |
| EP | 336620 A2 | 10/1989 |
| EP | 336620 B1 | 12/1993 |
| EP | 1351631 A1 | 10/2003 |
| EP | 1537840 A1 | 6/2005 |
| EP | 1608280 A2 | 12/2005 |
| JP | 63315049 A | 12/1988 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A2 | 6/2001 |
| JP | 2002087836 A2 | 3/2002 |
| JP | 2002233534 A2 | 8/2002 |
| WO | WO-9211814 A1 | 7/1992 |
| WO | WO-9520374 A1 | 8/1995 |
| WO | WO-9808442 A1 | 3/1998 |
| WO | WO-0051508 A1 | 9/2000 |
| WO | WO-0064388 A1 | 11/2000 |
| WO | WO-0113838 A1 | 3/2001 |
| WO | WO-02056806 A1 | 7/2002 |
| WO | WO-2005092023 A2 | 10/2005 |

OTHER PUBLICATIONS

Pacifico R.L., "Ultrasonic Energy in Phacoemulsification: Mechanical Cutting and Cavitation," Journal of Cataract & Refractive Surgery, 1994, vol. 20 (3), pp. 338-341.

Devine M.T., ed., "How to Set the Dials," in: Phacoemulsification Surgery, Pergamon Press, Chapter 2, 1991, pp. 7-28.

European Search Report for Application No. EP121915821, mailed on May 22, 2013, 6 pages.

European Search Report for Application No. EP07011327, mailed on Aug. 6, 2007, 2 pages.

International Preliminary Examination Report for Application No. PCT/US00/10989, mailed on Jul. 13, 2001, 9 pages.

International Preliminary Examination Report for Application No. PCT/US02/00471, mailed on Nov. 19, 2002, 2 pages.

International Preliminary Report on Patentability and Written Opinion for Application No. PCT/US2004/07318, mailed on Sep. 16, 2005, 4 pages.

International Preliminary Report on Patentability and Written Opinion for Application No. PCT/US2004/07477, mailed on Sep. 16, 2005, 4 pages.

International Preliminary Report on Patentability and Written Opinion for Application No. PCT/US2004/32690, mailed on Apr. 10, 2006, 6 pages.

International Preliminary Report on Patentability and Written Opinion for Application No. PCT/US2007/074704, mailed on Feb. 3, 2009, 8 pages.

International Search Report for Application No. PCT/US00/10989, mailed on Aug. 9, 2000, 3 pages.

International Search Report for Application No. PCT/US02/00471, mailed on May 22, 2002, 3 pages.

International Search Report for Application No. PCT/US2004/07318, mailed on Jun. 15, 2005, 1 page.

International Search Report for Application No. PCT/US2004/07477, mailed on Feb. 3, 2005, 1 page.

International Search Report for Application No. PCT/US2004/32690, mailed on Jan. 25, 2005, 3 pages.

International Search Report for Application No. PCT/US2007/074704, mailed on Feb. 4, 2008, 4 pages.

International Search Report for Application No. PCT/US98/01004, mailed on Jun. 9, 1998, 2 pages.

Ocusystem Operation Manual, May 1995, 79 pages.

Ophthalmology Times, Pulsar Cuts Phaco Time, Boosts Efficiency in Cataract Removal, Aug. 15, 1986, vol. 11 (16), Harcourt Brace Jovanovich, Inc., 1 page.

Supplementary European Search Report for Application No. EP01989937, mailed on Jul. 6, 2005, 2 pages.

Supplementary European Search Report for Application No. EP04719741, mailed on Jun. 25, 2010, 2 pages.

Supplementary European Search Report for Application No. EP04749368, mailed on Jun. 18, 2010, 4 pages.

Taylor W.F., et al., "Intraoperative Troubleshooting of an Advanced Phacoemulsification System," The Surgial Technologist, 1985, vol. 17 (2), pp. 11-14.

\* cited by examiner

OCCLUSION SENSED

MODULATED PULSED ULTRASONIC POWER DELIVERY SYSTEM AND METHOD

This application is a divisional of co-pending U.S. patent application Ser. No. 13/200,061, filed on Sep. 16, 2011, which is a divisional of U.S. patent application Ser. No. 12/005,865, filed on Dec. 28, 2007, now U.S. Pat. No. 8,020,565, which is a continuation of U.S. patent application Ser. No. 10/387,335, filed on Mar. 12, 2003, now U.S. Pat. No. 7,316,664, which is a continuation-in-part of U.S. patent application Ser. No. 10/278,775, filed on Oct. 21, 2002, now U.S. Pat. No. 7,077,820, all of which are hereby incorporated by reference.

BACKGROUND OF THE INVENTION

Field of the Invention

The present invention relates generally to the field of surgical tissue removal systems, and more specifically to modulated pulsed ultrasonic power delivery during surgical procedures such as phacoemulsification.

Description of the Related Art

Phacoemulsification surgery has been successfully employed in the treatment of certain ocular problems, such as cataracts. Phacoemulsification surgery utilizes a small corneal incision to insert the tip of at least one phacoemulsification handheld surgical implement, or handpiece. The handpiece includes a needle which is ultrasonically driven once placed within an incision to emulsify the eye lens, or break the cataract into small pieces. The broken cataract pieces may subsequently be removed using the same handpiece or another handpiece in a controlled manner. The surgeon may then insert lens implants in the eye through the incision. The incision is allowed to heal, and the results for the patient are typically significantly improved eyesight.

As may be appreciated, the flow of fluid to and from a patient through a fluid infusion or extraction system and power control of the phacoemulsification handpiece is critical to the procedure performed. Different medically recognized techniques have been utilized for the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens. Simultaneously with this emulsification, the handpiece provides a fluid for irrigation of the emulsified lens and a vacuum for aspiration of the emulsified lens and inserted fluids.

Currently available phacoemulsification systems include a variable speed peristaltic pump, a vacuum sensor, an adjustable source of ultrasonic power, and a programmable microprocessor with operator-selected presets for controlling aspiration rate, vacuum and ultrasonic power levels. A phacoemulsification handpiece is interconnected with a control console by an electric cable for powering and controlling the piezoelectric transducer. Tubing provides irrigation fluid to the eye and enables withdrawal of aspiration fluid from an eye through the handpiece. The hollow needle of the handpiece may typically be driven or excited along its longitudinal axis by the piezoelectric effect in crystals created by an AC voltage applied thereto. The motion of the driven crystal is amplified by a mechanically resonant system within the handpiece such that the motion of the needle connected thereto is directly dependent upon the frequency at which the crystal is driven, with a maximum motion occurring at a resonant frequency. The resonant frequency is dependent in part upon the mass of the needle interconnected therewith, which is typically vibrated by the crystal.

A typical range of frequency used for phacoemulsification handpiece is between about 25 kHz to about 50 kHz. A frequency window exists for each phacoemulsification handpiece that can be characterized by specific handpiece impedance and phase. The aforementioned frequency window is bounded by an upper frequency and a lower cutoff frequency. The center of this window is typically the point where the handpiece electrical phase reaches a maximum value.

Handpiece power transfer efficiency is given by the formula $(V*I)(COS\ \Phi)$, where $\Phi$ is the phase angle. Using this power transfer efficiency equation, the most efficient handpiece operating point occurs when the phase is closest to 0 degrees. Thus optimum handpiece power transfer efficiency requires controlling power frequency to achieve a phase value as close to zero degrees as possible. Achieving this goal is complicated by the fact that the phase angle of the ultrasonic handpiece also depends on transducer loading. Transducer loading occurs through the mechanically resonant handpiece system, including the needle. Contact by the needle with tissue and fluids within the eye create a load on the piezoelectric crystals with concomitant change in the operating phase angle.

Consequently, phase angles are determined and measured at all times during operation of the handpiece to adjust the driving circuitry, achieve an optimum phase angle, and effect constant energy transfer into the tissue by the phacoemulsification handpiece. Automatic tuning of the handpiece may be provided by monitoring the handpiece electrical signals and adjusting the frequency to maintain consistency with selected parameters. Control circuitry for a phacoemulsification handpiece can include circuitry for measuring the phase between the voltage and the current, typically identified as a phase detector. Difficulties may arise if phase shift is measured independent of the operating frequency of the phacoemulsification handpiece, because phase shift depends on handpiece operating frequency, and time delay in the measurement thereof requires complex calibration circuitry to provide for responsive tuning of the handpiece.

Power control of the phacoemulsification handpiece is highly critical to successful phacoemulsification surgery. Certain previous systems address the requirements of power control for a phacoemulsification handpiece based on the phase angle between voltage applied to a handpiece piezoelectric transducer and the current drawn by the piezoelectric transducer and/or the amplitude of power pulses provided to the handpiece. The typical arrangement is tuned for the particular handpiece, and power is applied in a continuous fashion or series of solid bursts subject to the control of the surgeon/operator. For example, the system may apply power for 150 ms, then cease power for 350 ms, and repeat this on/off sequence for the necessary duration of power application. In this example, power is applied through the piezoelectric crystals of the phacoemulsification handpiece to the needle causing ultrasonic power emission for 150 ms, followed by ceasing application of power using the crystals, handpiece, and needle for 350 ms. It is understood that while power in this example is applied for 150 ms, this application of power includes application of a sinusoidal waveform to the piezoelectric crystals at a frequency of generally between about 25 kHz and 50 kHz and is thus not truly "constant." Application of power during this 150 ms period is defined as a constant application of a 25 kHz to 50 kHz sinusoid. In certain circumstances, the surgeon/operator may wish to apply these power bursts for a duration of time, cease application of power, then reapply at this or another power setting. The frequency and duration of the burst is typically controllable, as is the length of the stream of bursts applied to the affected area. The time period where power is not applied enable cavitation in the affected area whereby broken sections may be removed using aspiration provided by the handpiece or an aspiration apparatus.

Additionally, the surgeon operator may wish to employ certain known procedures, such as a "sculpt" procedure to break the lens, or a "chop" procedure to collect the nucleus and maintain a strong hold on the broken pieces. These specialized "chop or quadrant removal" procedures typically entail applying power or energy in a constant span of anywhere from approximately 50 milliseconds to 200 milliseconds in duration.

The on/off application of power facilitates breaking the cataract into pieces and relatively efficient removal thereof. The ultrasonically driven needle in a phacoemulsification handpiece becomes warm during use, resulting from frictional heat due in part to mechanical motion of the phacoemulsification handpiece tip. In certain circumstances, it has been found that the aforementioned method of applying power to the affected region in a continuous mode can produce a not insignificant amount of heat in the affected area. Irrigation/aspiration fluids passing through the needle may be used to dissipate this heat, but care must be taken to avoid overheating of eye tissue during phacoemulsification, and in certain procedures fluid circulation may not dissipate enough heat. The risk of damaging the affected area via application of heat can be a considerable negative side effect.

Further, the application of power in the aforementioned manner can in certain circumstances cause turbulence and/or chatter, as well as cause significant flow issues, such as requiring considerable use of fluid to relieve the area and remove particles. Also, the application of constant groups of energy can cause nuclear fragments to be pushed away from the tip of the handpiece because of the resultant cavitation from the energy applied. Collecting and disposing of fragments in such a cavitation environment can be difficult in many circumstances. These resultant effects are undesirable and to the extent possible should be minimized.

One system that has been effectively employed in this environment is disclosed in U.S. patent application Ser. No. 10/278,775, inventors Kadziauskas et al, filed Oct. 21, 2002 and assigned to Advanced Medical Optics, Inc., the assignee of the present application. The '775 application provides for ultrasonic power delivery using relatively brief applications of power interspersed by short pauses over a long period, each long period of power application followed by a lengthy rest period. This design enables application of energy without the heat problems associated with previous constant applications of power.

Certain developments have demonstrated that beneficial effects beyond those demonstrated in the design of the '775 application may be obtained by employing those beneficial effects associated with cavitation in the environment described. Certain types of cavitation can provide for improved occlusion breakup in some conditions. Understanding and employing the beneficial effects of cavitation may thus provide for enhanced removal of the nucleus in a phacoemulsification procedure without the heat associated with the previous designs.

Based on the foregoing, it would be advantageous to provide a system that employs those benefits associated with cavitation and minimizes those drawbacks associated with previous tissue removal systems.

SUMMARY OF THE INVENTION

According to one aspect of the present design, there is presented a method for delivering energy during a surgical procedure, comprising applying energy during a modulated energy delivery period. The modulated energy delivery period comprises applying energy during a plurality of short burst periods, the short burst periods comprising a high energy burst period followed a predetermined time thereafter by a nonzero low energy burst period.

These and other objects and advantages of all aspects of the present invention will become apparent to those skilled in the art after having read the following detailed disclosure of the preferred embodiments illustrated in the following drawings.

DESCRIPTION OF THE DRAWINGS

The present invention is illustrated by way of example, and not by way of limitation, in the figures of the accompanying drawings in which.

DETAILED DESCRIPTION OF THE INVENTION

Device.

Figure 1:
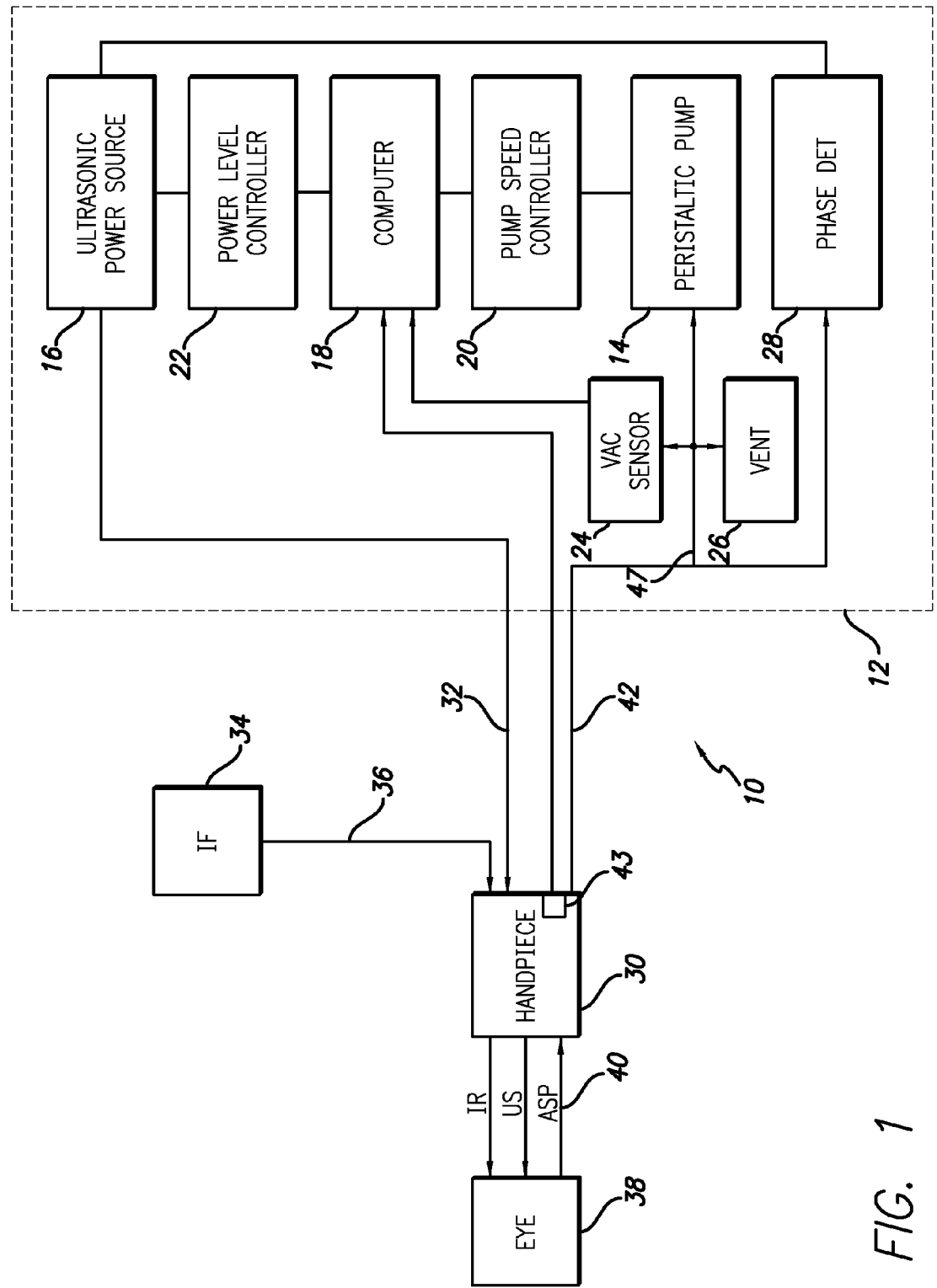
FIG. 1 is a functional block diagram of a phacoemulsification system in accordance with an aspect of the present invention.

FIG. 1 illustrates a phacoemulsification system in block diagram form, indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the input side of peristaltic pump 14. Suitable venting is provided by vent 26.

A phase detector 28 provides an input to computer 18 representing a phase shift between a sine wave representation of the voltage applied to a handpiece/needle 30 and the resultant current into the handpiece 30. The block representation of the handpiece 30 includes a needle and electrical means, typically a piezoelectric crystal, for ultrasonically vibrating the needle. The control unit 12 supplies power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38. Alternatively, the irrigation source may be routed to the eye 38 through a separate pathway independent of the handpiece. The eye 38 is aspirated by the control unit peristaltic pump 14 through line/handpiece needle 40 and line 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 2:
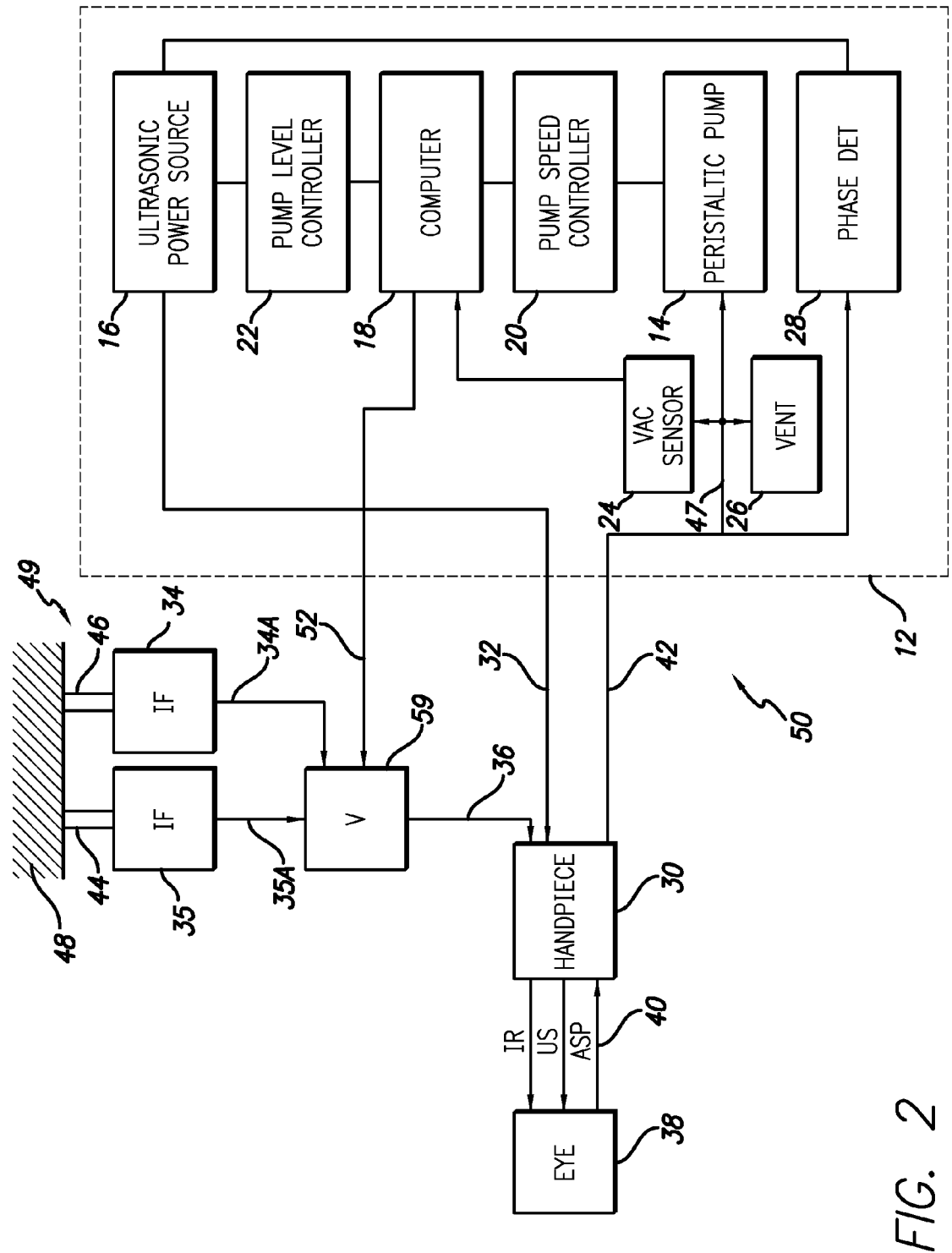
FIG. 2 is a functional block diagram of an alternative aspect of a phacoemulsification system including apparatus for providing irrigation fluid at more than one pressure to a handpiece.

FIG. 2 shows an alternative phacoemulsification system 50 incorporating all of the elements of the system 10 shown in FIG. 1, with identical reference characters identifying components, as shown in FIG. 1. In addition to the irrigation fluid source 34, a second irrigation fluid source 35 is provided with the sources 34, 35 being connected to the line 36 entering the handpiece/needle 30 through lines 34a, 35a, respectively, and to a valve 59. The valve 59 functions to alternatively connect line 34A and source 34 and line 35A and source 35 with the handpiece/needle 30 in response to a signal from the power level controller 22 through a line 52.

As shown, irrigation fluid sources 34, 35 are disposed at different heights above the handpiece/needle 30 providing a means for introducing irrigation fluid to the handpiece at a plurality of pressures, the head of the fluid in the container 35 being greater than the head of fluid in the container 34. A harness 49, including lines of different lengths 44, 46, when connected to the support 48, provides a means for disposing the containers 34, 35 at different heights over the handpiece/needle 30.

The use of containers for irrigation fluids at the various heights is representative of the means for providing irrigation fluids at different pressures, and alternatively, separate pumps may be provided with, for example, separate circulation loops (not shown). Such containers and pumps can provide irrigation fluid at discrete pressures to the handpiece/needle 30 upon a command from the power controller 22.

Operation.

Figure 3:
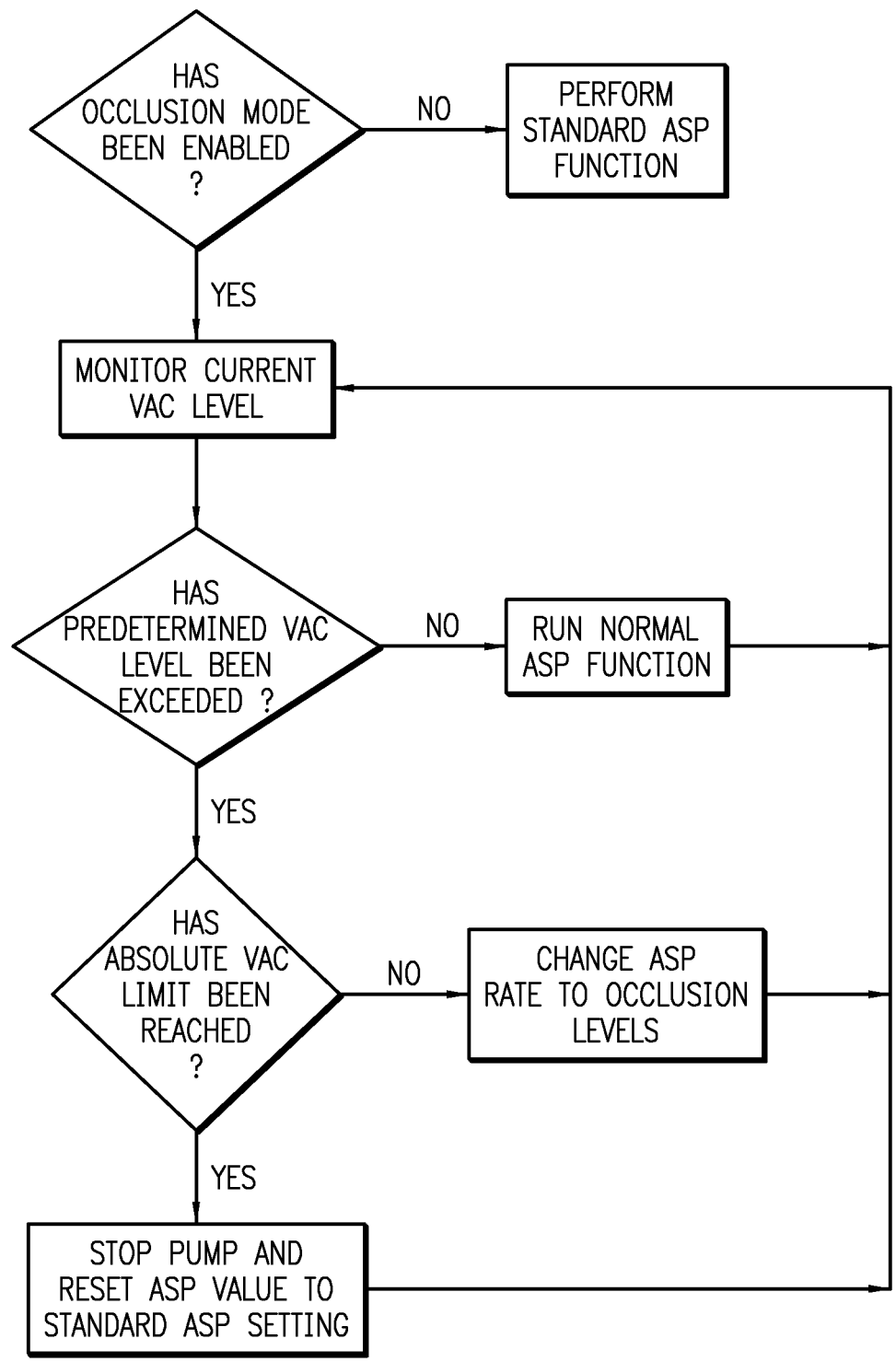
FIG. 3 is a flow chart illustrating the operation Of the occluded-unoccluded mode of the phacoemulsification system with variable aspiration rates.

The computer 18 responds to preset vacuum levels in input line 47 to peristaltic pump 14 by means of signals from the previously mentioned vacuum sensor 24. Operation of the control unit in response to the occluded-unoccluded condition of handpiece 30 is shown in the flow diagram of FIG. 3. As shown in FIG. 3, if the handpiece aspiration line 40 becomes occluded, the vacuum level sensed by vacuum sensor 24 may increase. The computer 18 may provide operator-settable limits for aspiration rates, vacuum levels and ultrasonic power levels. As illustrated in FIG. 3, when the vacuum level sensed by vacuum sensor 24 reaches a predetermined level as a result of occlusion of the handpiece aspiration line 40, computer 18 provides signals to pump speed controller 20 to change the speed of the peristaltic pump 14 which, in turn, changes the aspiration rate. Depending upon the characteristics of the material occluding handpiece/needle 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

Figure 4:
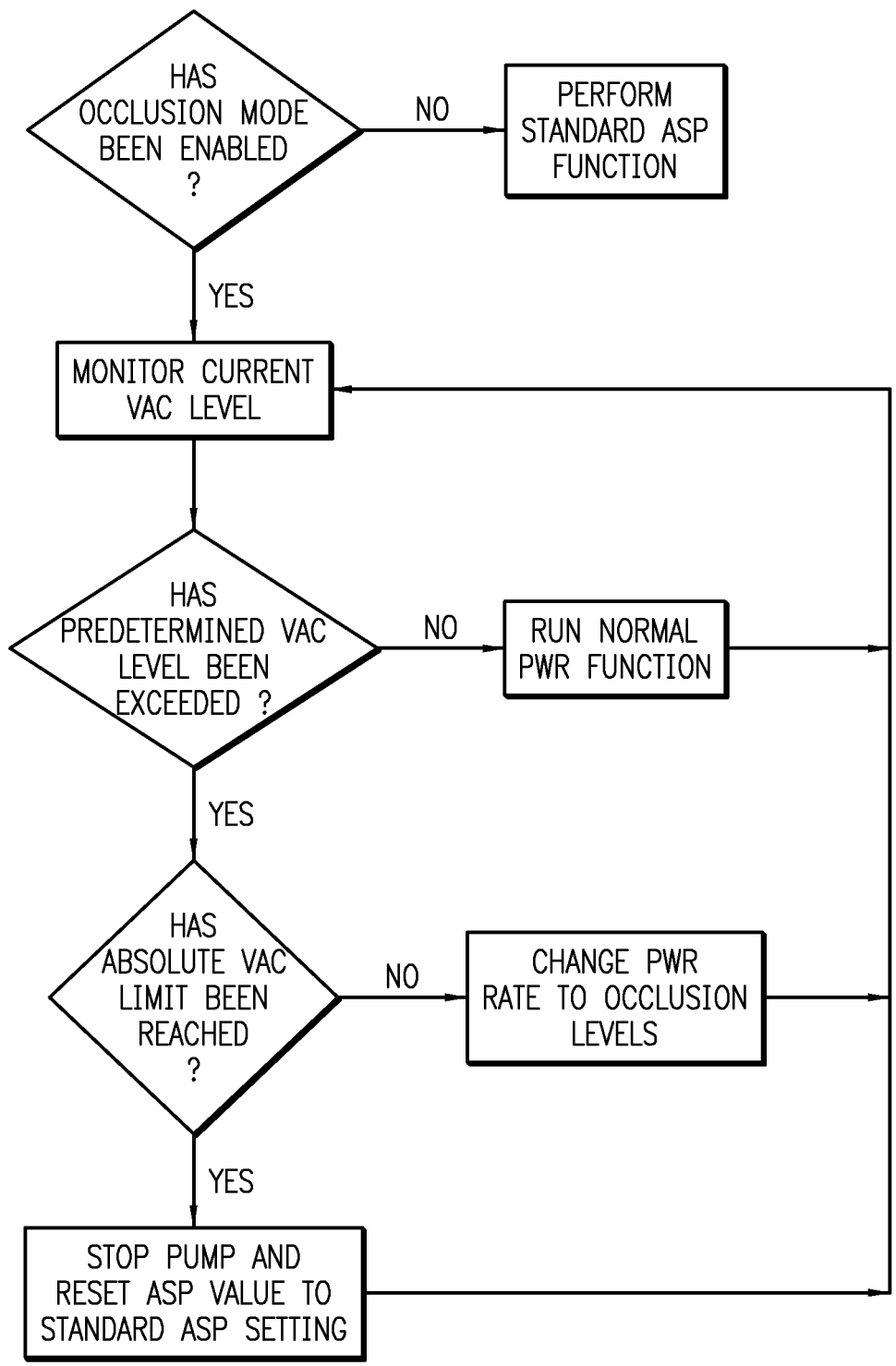
FIG. 4 is a flow chart illustrating the operation Of the occluded-unoccluded mode of the phacoemulsification system with variable ultrasonic power levels.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 4 illustrates in flow diagram form a basic form of control of the ultrasonic power source power level using computer 18 and power level controller 22. The flow diagram of FIG. 4 corresponds to the flow diagram of FIG. 3 but varies the phacoemulsification parameter of the ultrasonic power level.

Figure 8:
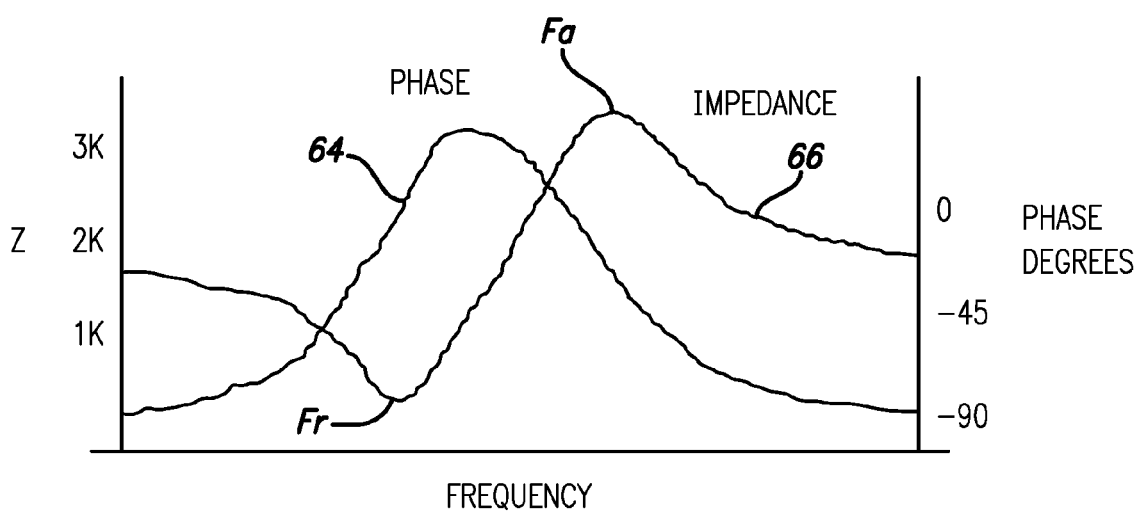
FIG. 8 is a plot of the phase relationship and the impedance of a typical piezoelectric phacoemulsification handpiece.

The impedance of the typical phacoemulsification handpiece varies with frequency, or in other words, the handpiece is reactive. Dependence of typical handpiece phase and impedance as a function of frequency is shown in FIG. 8. In FIG. 8, curve 64 represents the phase difference between current and voltage of the handpiece as function frequency and curve 66 shows the change in impedance of the handpiece as a function of frequency. The impedance exhibits a low at "Fr" and a high "Fa" for a typical range of frequencies, such as in the range of approximately 25 kHz to approximately 50 kHz.

Figure 7:
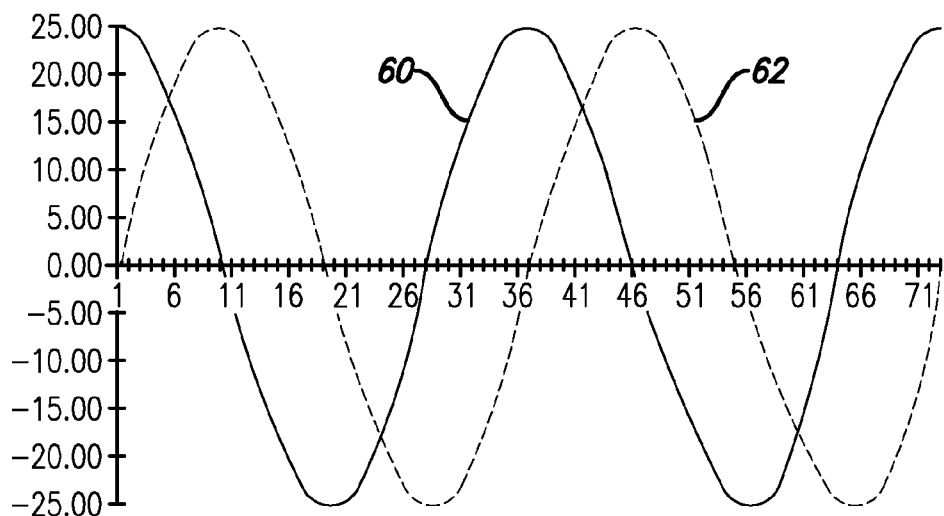
FIG. 7 is a plot of the 90 degree phase shift between the sine wave representation of the voltage applied to a piezoelectric phacoemulsification handpiece and the resultant current into the handpiece.

Automatic tuning of the handpiece typically requires monitoring the handpiece electrical signals and adjusting the frequency to maintain a consistency with selected parameters. To compensate for a load occurring at the tip of the phacoemulsification handpiece, the drive voltage to the handpiece can be increased while the load is detected and then decreased when the load is removed. This phase detector is typically part of the controller in this type of system. In such conventional phase detectors, the typical output is a voltage as proportional to the difference in alignment of the voltage and the current waveform, for example, −90 degrees as shown in FIG. 7. As shown in FIG. 8, while using the handpiece, the waveform varies in phase and correspondingly the output waveform also varies.

Heretofore, the standard technique for measuring electrical phase has been to read a voltage proportional to phase and also to frequency. This type of circuit may be calibrated for use with a single frequency. Changing the frequency may cause the calibration data to be incorrect. As also seen in single frequency systems, corrected phase value will drift due to variation in the circuit parameters.

Figure 9:
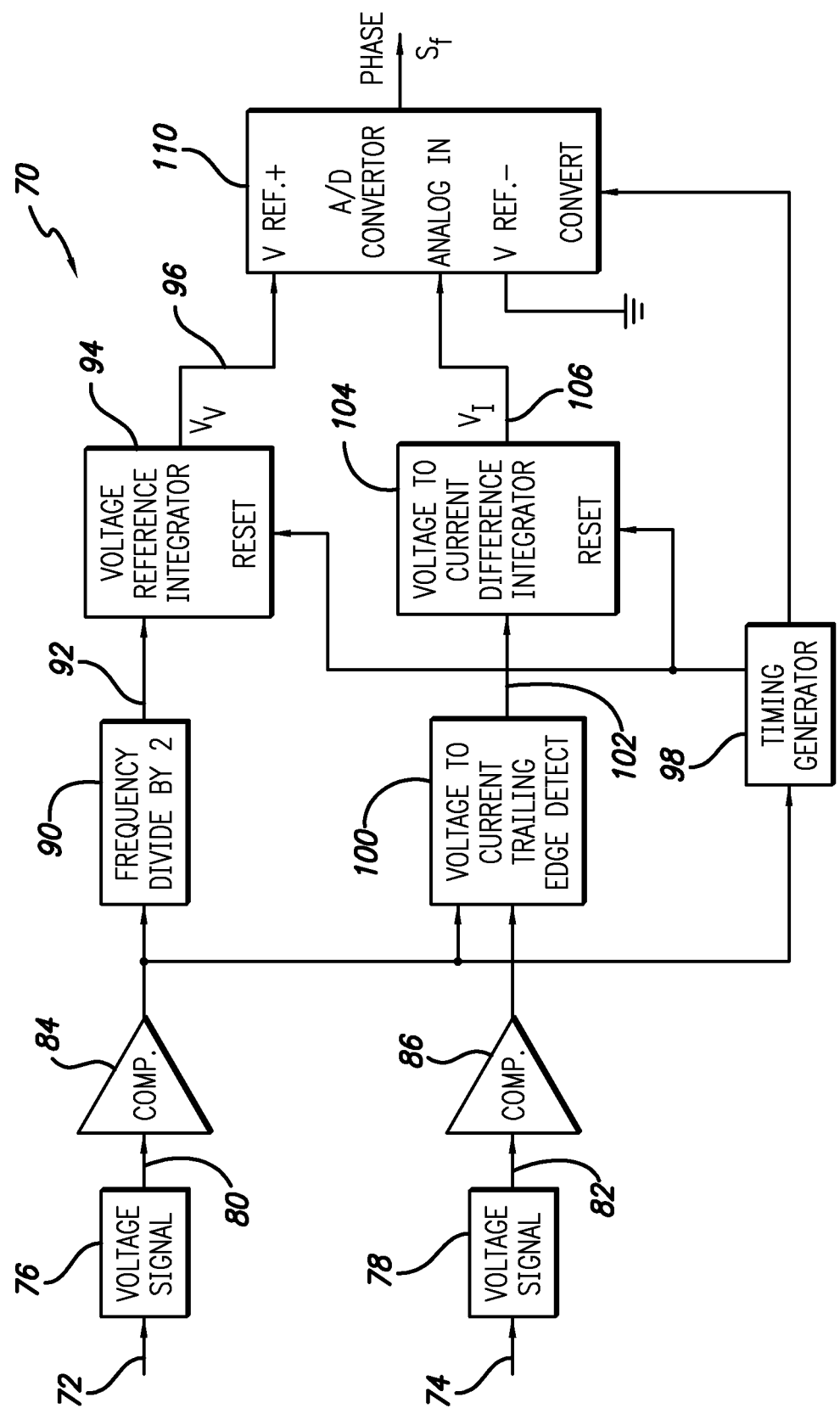
FIG. 9 is a block diagram of improved phase detector circuitry suitable for performing a method in accordance with the present invention.

One other available approach utilizes a microprocessor to compare the value of the phase detector output with that of a frequency detector and compute the true phase. This approach is fairly complex and is subject to drift of the individual circuits as well as resolution limitations. A block diagram 70 as shown in FIG. 9 is representative of an improved phase detector suitable for performing in accordance with the design. Each of the function blocks shown comprises conventional state-of-the-art circuitry of typical design and components for producing the function represented by each block as hereinafter described.

The system converts voltage input 72 and current 74 from a phacoemulsification handpiece 30 to an appropriate signal using an attenuator 76 on the voltage signal to the phacoemulsification handpiece, and a current sense resistor 78 and fixed gain amplifier for the handpiece 30 current. Thereafter, the system passes an AC voltage signal 80 and AC current signal 82 to comparators 84, 86 which convert the analog representations of the phacoemulsification voltage and current to logic level clock signals.

The system feeds output from the comparator 84 into a D flip flop integrated circuit 90 configured as a frequency divide by 2. The system then feeds output 92 of the integrated circuit 90 into an operational amplifier configured as an integrator 94. The output 96 of the integrator 94 is a sawtooth waveform of which the final amplitude is inversely proportional to the handpiece frequency. A timing generator 98 uses a clock synchronous with the voltage signal to generate A/D converter timing, as well as timing to reset the integrators at the end of each cycle. The system feeds this signal into the voltage reference of an A/D converter via line 96.

The voltage leading edge to current trailing edge detector 100 uses a D flip flop integrated circuit to isolate the leading edge of the handpiece voltage signal. This signal is used as the initiation signal to start the timing process between the handpiece 30 voltage and handpiece 30 current. The output 102 of the leading edge to current trailing edge detector 100 is a pulse proportional to the time difference in occurrence of the leading edge of the handpiece 30 voltage waveform and the falling edge of the handpiece current waveform.

The system uses another integrator circuit 104 for the handpiece phase signal 102 taken from the leading edge to current trailing edge detector 100. Output 106 of the integrator circuit 104 is a sawtooth waveform in which the peak amplitude is proportional to the time difference in the onset of leading edge of the phacoemulsification voltage and the trailing edge of the onset of the handpiece current waveform. The system feeds output 106 of the integrator circuit 104 into the analog input or an A/D (analog to digital converter) integrated circuit 110. The positive reference input 96 to the A/D converter 110 is a voltage that is inversely proportional to the frequency of operation. The phase voltage signal 96 is proportional to the phase difference between the leading edge of the voltage onset, and the trailing edge of the current onset, as well as inversely proportional to the frequency of operation. In this configuration, the two signals frequency voltage reference 96 and phase voltage 106 track each other over the range of frequencies, so that the output of the A/D converter 110 produces the phase independent of the frequency of operation.

In this arrangement, the system computer 18 (see FIGS. 1 and 2) is provided with a real time digital phase signal wherein 0 to 255 counts will consistently represent 0 to 359 degrees of phase. No form of calibration is necessary since the measurements are consistent despite the frequencies utilized. For example, using AMPs operation frequencies of 38 kHz and 47 kHz and integrator having a rise time of $150 \times 10^5$ V/sec and an 8 bit A/D converter having 256 counts, a constant ratio is maintained and variation in frequency does not affect the results. This shown in the following examples.

EXAMPLE 1

38 KHz Operation

Period of 1 clock cycle=1/F @38 KHz=26.32 times $10^{-6}$ S

Portion of one period for I=90 deg=26.32 times $10^{-6}$ S

Divided by 4=6.59 times $10^{-6}$ S

Integrator output for one reference cycle=(150 times $10^3$ V/S) times (26.32 times $10^{-6}$ S)=3.95 Volts Integrator output from 90 degree cycle duration=(150 times $10^3$ V/S) times (6.59 times $10^{-6}$ S)=0.988 Volts Resulting Numerical count from A/D converter=3.95 Volts/256 counts=0.0154 Volts per count Actual Number of A/D counts for 90 deg at 38 KHz=0.988/0.0154=64 counts

EXAMPLE 2

47 KHz Operation

Period of 1 clock cycle=1/F @47 KHz=21.28 times $10^{-6}$ S

Portion of one period for I=90 deg=21.28 times $10^{-6}$ S

Divided by 4=5.32 times $10^{-6}$ S

Integrator output for one reference cycle=(150 times $10^3$ V/S) times (21.28 times $10^{-6}$ S)=3.19 volts Integrator output from 90 degree cycle duration=(150 times $10^3$ V/S) times (5.32 times $10^{-6}$ S)=0.798 Volts Resulting Numerical count from A/D converter=3.19 Volts/256 counts=0.0124 Volts per count Actual Number of A/D counts for 90 deg at 47 KHz=0.798/0.0124=64 counts This represents the baseline operation of the present system, namely the ability to tune the phacoemulsification handpiece to a generally acceptable level.

Energy Delivery.

Figure 5:
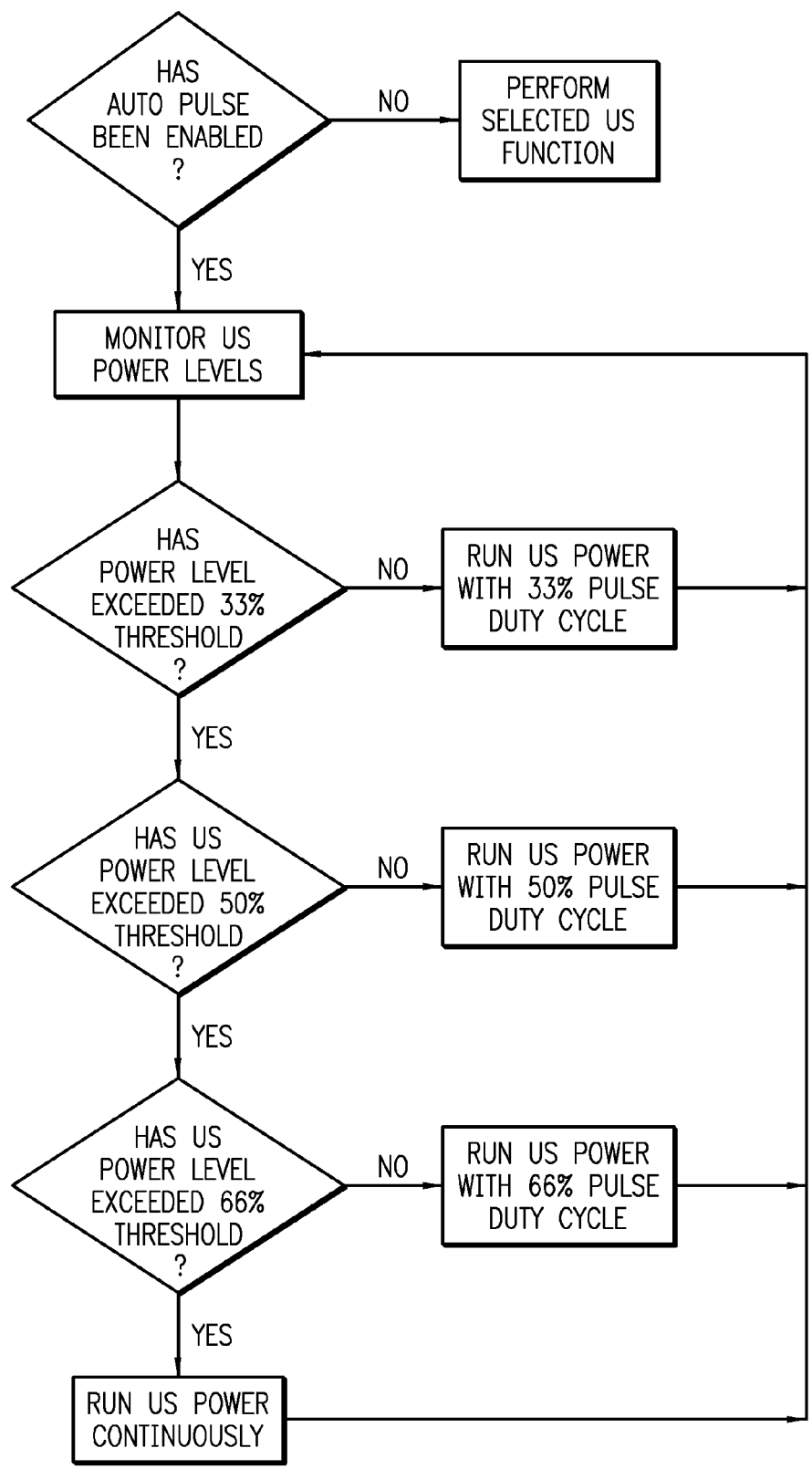
FIG. 5 is a flow chart illustrating the operation of a variable duty cycle pulse function of the phacoemulsification system.

The following sections deal generally with the types of delivery of microburst energy generally employed to effectively carry out the phacoemulsification procedure. With reference to FIG. 5, there is shown a flow diagram depicting basic control of the ultrasonic power source 16 to produce varying pulse duty cycles as a function of selected power levels. Each power pulse may have a duration of less than 20 milliseconds. As shown in FIG. 5, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33, 50 and 66 have been illustrated in FIG. 5, it should be understood that other percentage levels can be selected as well as various duty cycles to define different duty cycle shift points. The pulse duration in this arrangement may be less than 20 milliseconds. This control along with the tracking mechanism herein described enables bursts of energy less than 20 milliseconds in duration.

Figure 13:
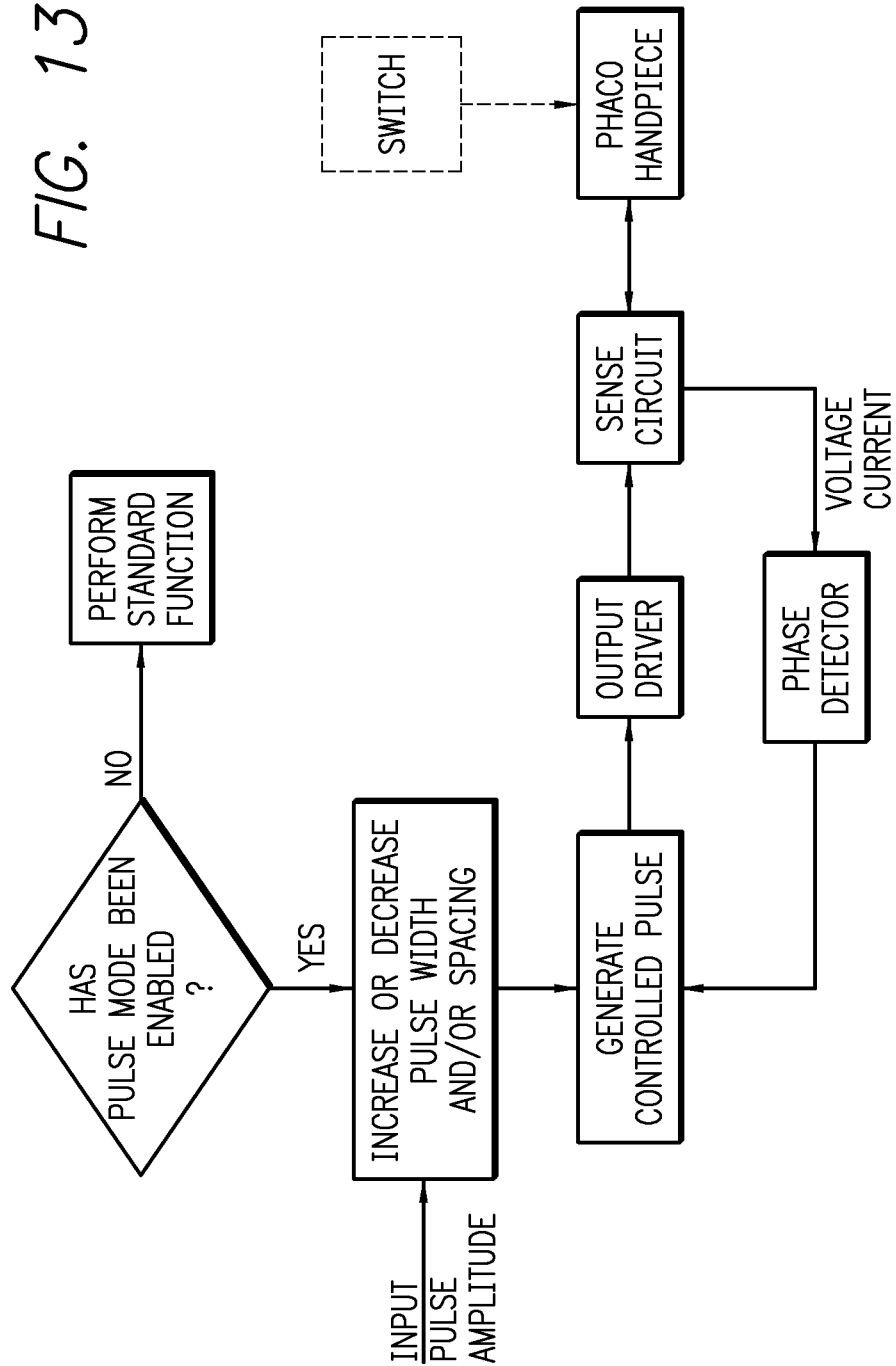
FIG. 13 is a function block control diagram of a pulse control phacoemulsification system.

With reference to FIG. 13, a rapid pulse duration of less than 20 milliseconds is provided with adequate energy to cut the tissue with kinetic or mechanical energy. The ultrasonic energy pulse may then be turned off long enough to significantly decrease the resultant heat level before the next pulse is activated. A surgeon/operator may vary the pulse amplitude in a linear manner via the switch 143 and the control unit 22 in response to the selected pulse amplitude, irrigation and aspiration fluid flow rates, controlling a pulse duty cycle. As hereinabove noted, an off duty duration or cycle is provided to ensure heat dissipation before a subsequent pulse is activated. In this way, increased amplitude will increase tip acceleration and thus heat dissipation level for tissue damaging heat generation. That is, the surgeon/operator can use linear power control to select the correct acceleration necessary to cut through the tissue density while the control unit provides a corresponding variation in pulse width of less than 20 milliseconds and "off time" to prevent tissue de-compensation from heat. The control unit is programmed depending on the phacoemulsification handpiece chosen (total wattage) or the phacoemulsification tip (dimensions, weight). This use of rapid pulsing is similar to how lasers operate with very short duration pulses. Pulses in this configuration may have a repetition rate of between about 25 and 2000 pulses per second.

With reference to FIG. 5, if the handpiece aspiration line 38 is occluded, the vacuum level sensed by the vacuum sensor 24 will increase. The computer 18 has operator-settable limits for controlling which of the irrigation fluid supplies 32, 33 will be connected to the handpiece 30. While two irrigation fluid sources, or containers 32, 33 are shown, any number of containers may be utilized.

Figure 6:
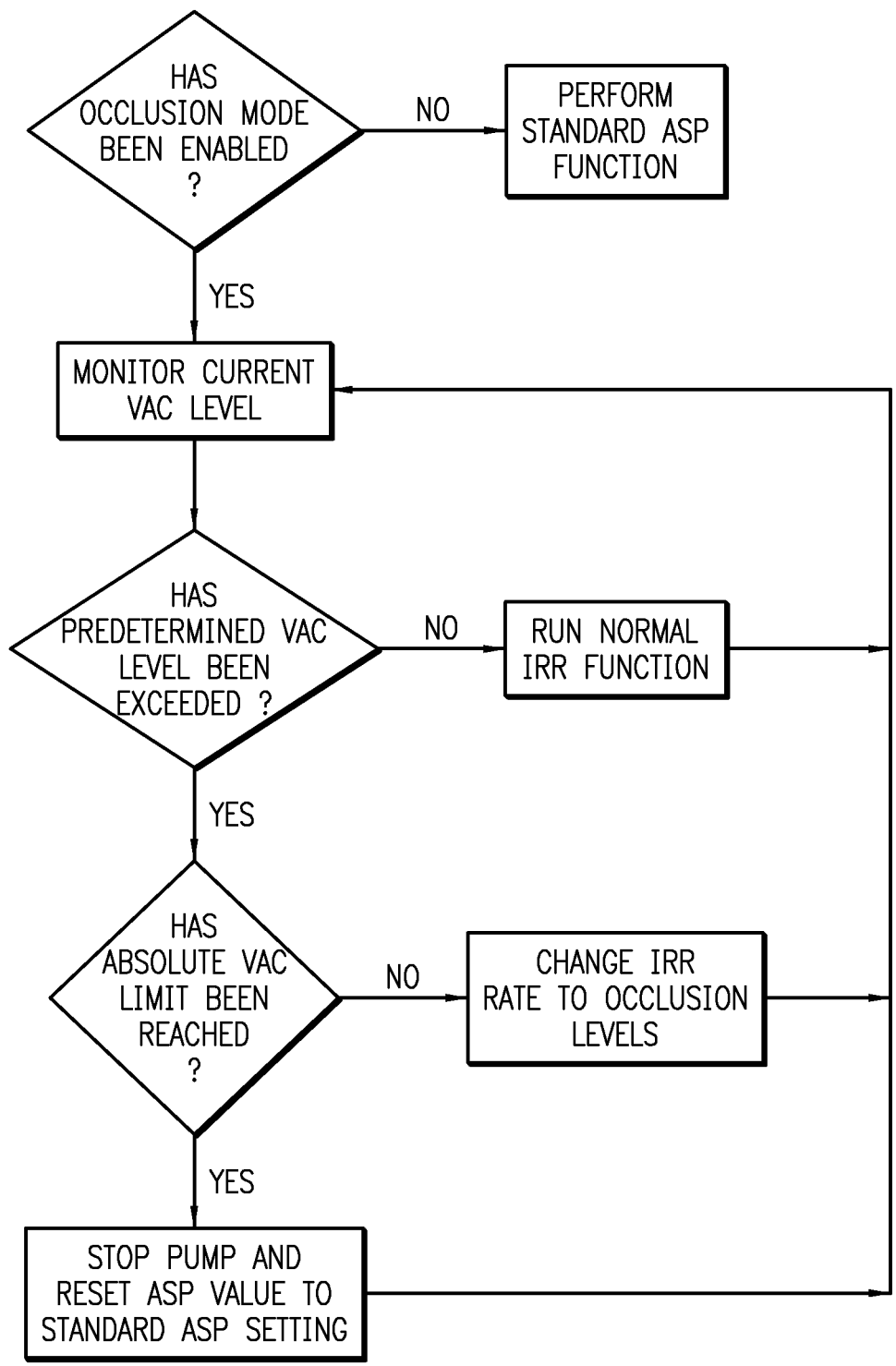
FIG. 6 is a flow chart illustrating the operation of the occluded-unoccluded mode of the phacoemulsification system with variable irrigation rates.

As shown in FIG. 6, when the vacuum level by the vacuum sensor 24 reaches a predetermined level, as a result of occlusion of the aspiration handpiece line 38, the computer controls the valve 38 causing the valve to control fluid communication between each of the containers 34, 35 and the handpiece/needle 30.

Depending upon the characteristics of the material occluding the handpiece/needle 30, as hereinabove described and the needs and techniques of the physician, the pressure of irrigation fluid provided the handpiece may be increased or decreased. As occluded material is cleared, the vacuum sensor 24 may register a drop in the vacuum level causing the valve 38 to switch to a container 34, 35, providing pressure at an unoccluded level.

More than one container may be utilized, such as three containers (not shown) with the valve interconnecting to select irrigation fluid from any of the three containers, as hereinabove described in connection with the container system.

In addition to changing phacoemulsification handpiece/needle 30 parameter as a function of vacuum, the occluded or unoccluded state of the handpiece can be determined based on a change in load sensed by a handpiece/needle by way of a change in phase shift or shape of the phase curve. A plot of phase angle as a function of frequency is shown in FIG. 10 for various handpiece 30 loading, a no load (max phase), light load, medium load and heavy load.

Figure 10:
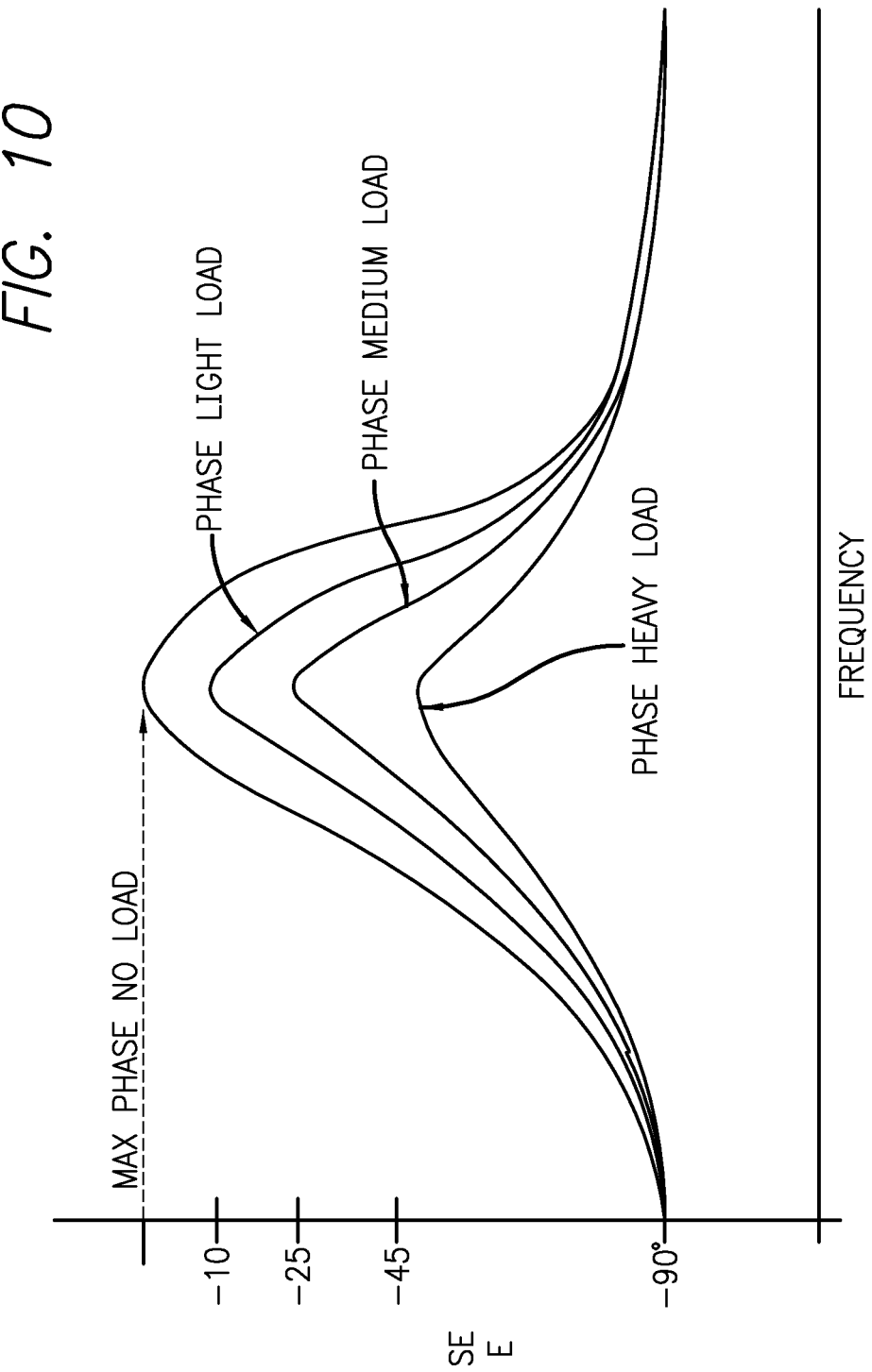
FIG. 10 is a plot of phase relationship as a function of frequency for various handpiece/needle loading.
Figure 11:
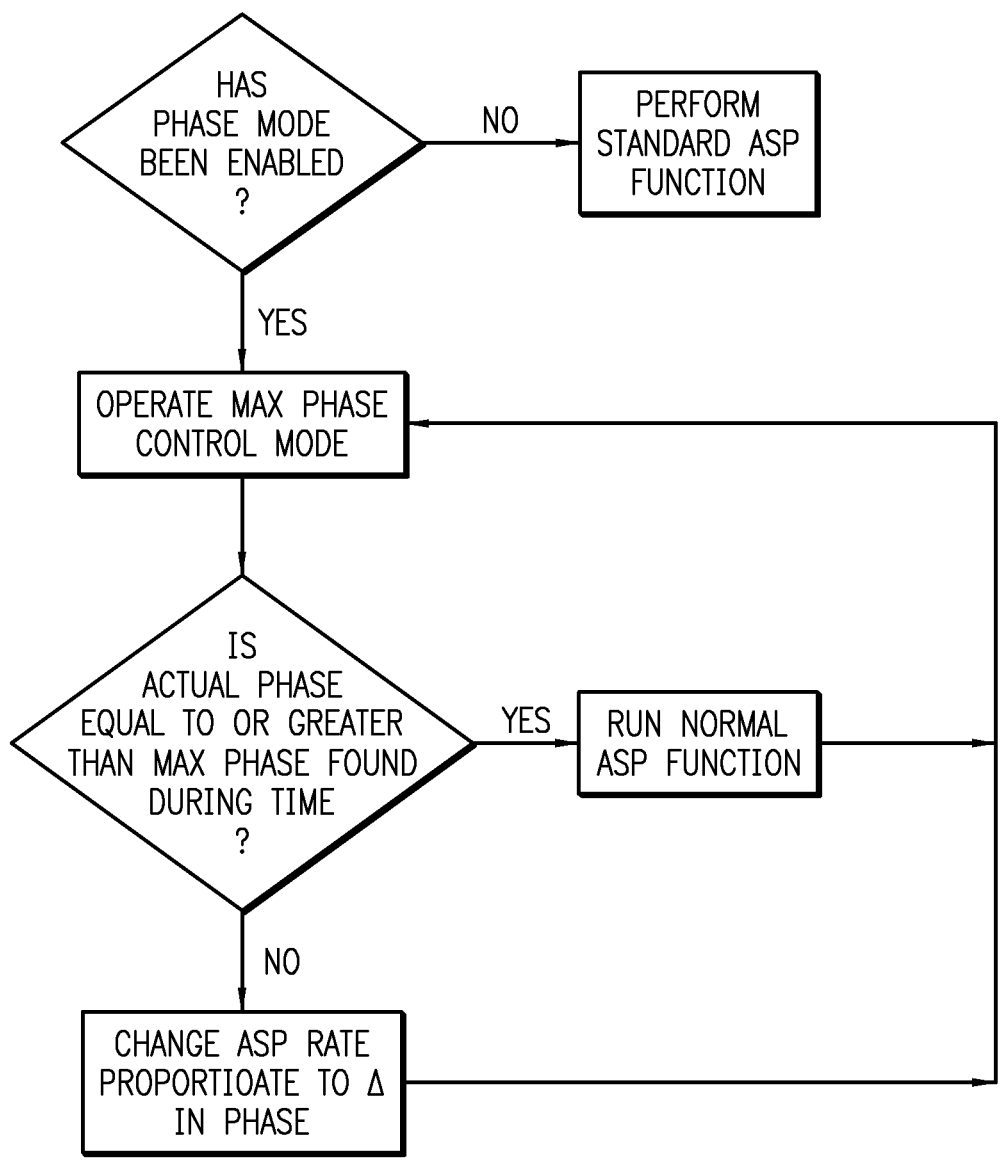
FIG. 11 is a function block diagram of a phase control phacoemulsification system utilizing phase angles to control handpiece/needle parameters with max phase mode operation.
Figure 12:
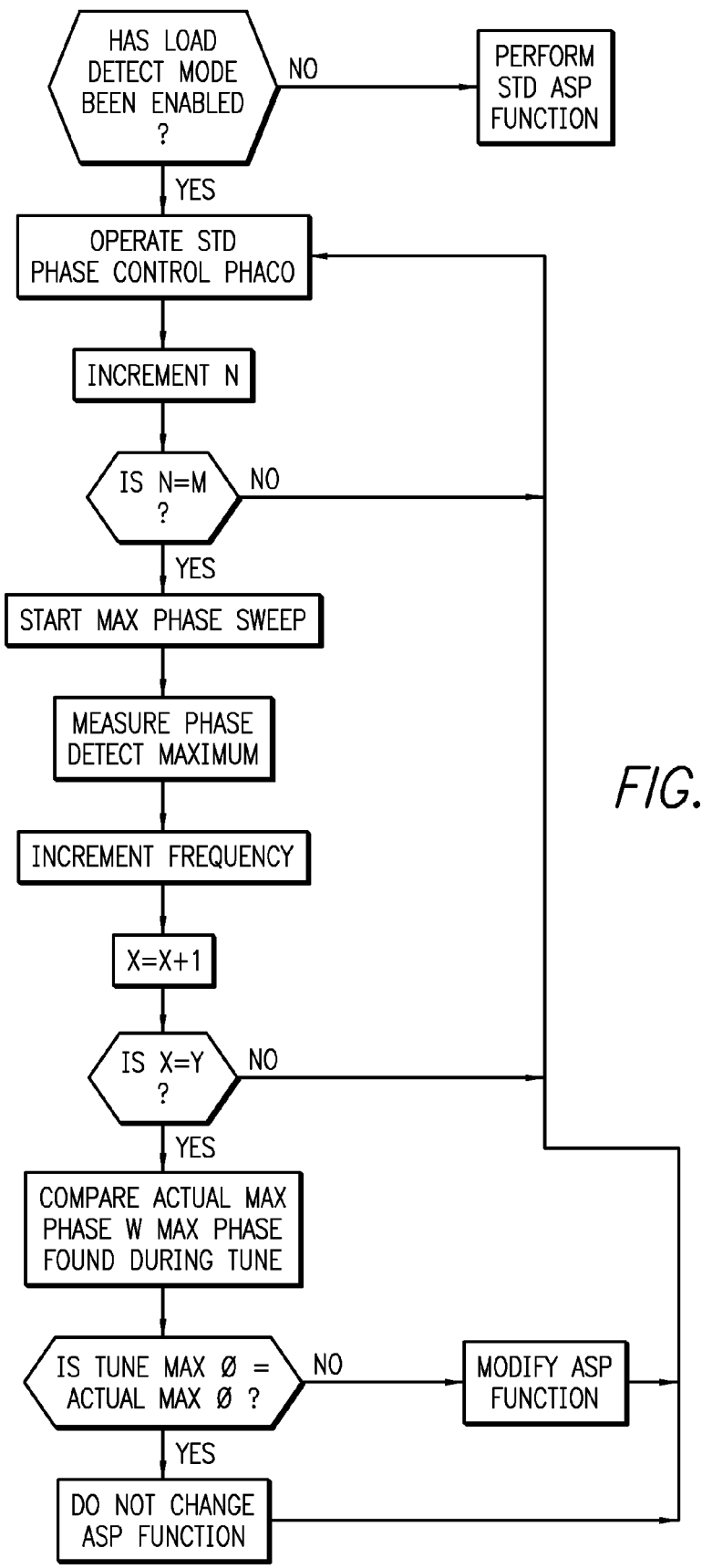
FIG. 12 is a function block control diagram of a phase control phacoemulsification system utilizing phase angles to control handpiece/needle parameters with a load detect method.

With reference to FIG. 11, representing max phase mode operation, the actual phase is determined and compared to the max phase. If the actual phase is equal to, or greater than, the max phase, normal aspiration function is performed. If the actual phase is less than the max phase, the aspiration rate is changed, with the change being proportionate to the change in phase. FIG. 12 represents operation at less than max load in which load (see FIG. 10) detection is incorporated into the operation.

As represented in FIG. 11, representing max phase mode operation, if the handpiece aspiration line 40 is occluded, the phase sensed by phase detector sensor 28 will decrease (see FIG. 10). The computer 18 has operator-settable limits for aspiration rates, vacuum levels and ultrasonic power levels. As illustrated in FIG. 11, when the phase sensed by phase detector 28 reaches a predetermined level as a result of occlusion of the handpiece aspiration line 40, computer 18 instructs pump speed controller 20 to change the speed of the peristaltic pump 14 which, in turn, changes the aspiration rate.

Depending upon the characteristics of the material occluding handpiece/needle 30, the speed of the peristaltic pump 14 can either be increased or decreased. When the occluding material is broken up, the phase detector 28 registers an increase in phase angle, causing computer 18 to change the speed of peristaltic pump 14 to an unoccluded operating speed.

In addition to changing the phacoemulsification parameter of aspiration rate by varying the speed of the peristaltic pump 14, the power level and/or duty cycle of the ultrasonic power source 16 can be varied as a function of the occluded or unoccluded condition of handpiece 30 as hereinabove described.

Microburst Enhanced Operation.

Figure 14:
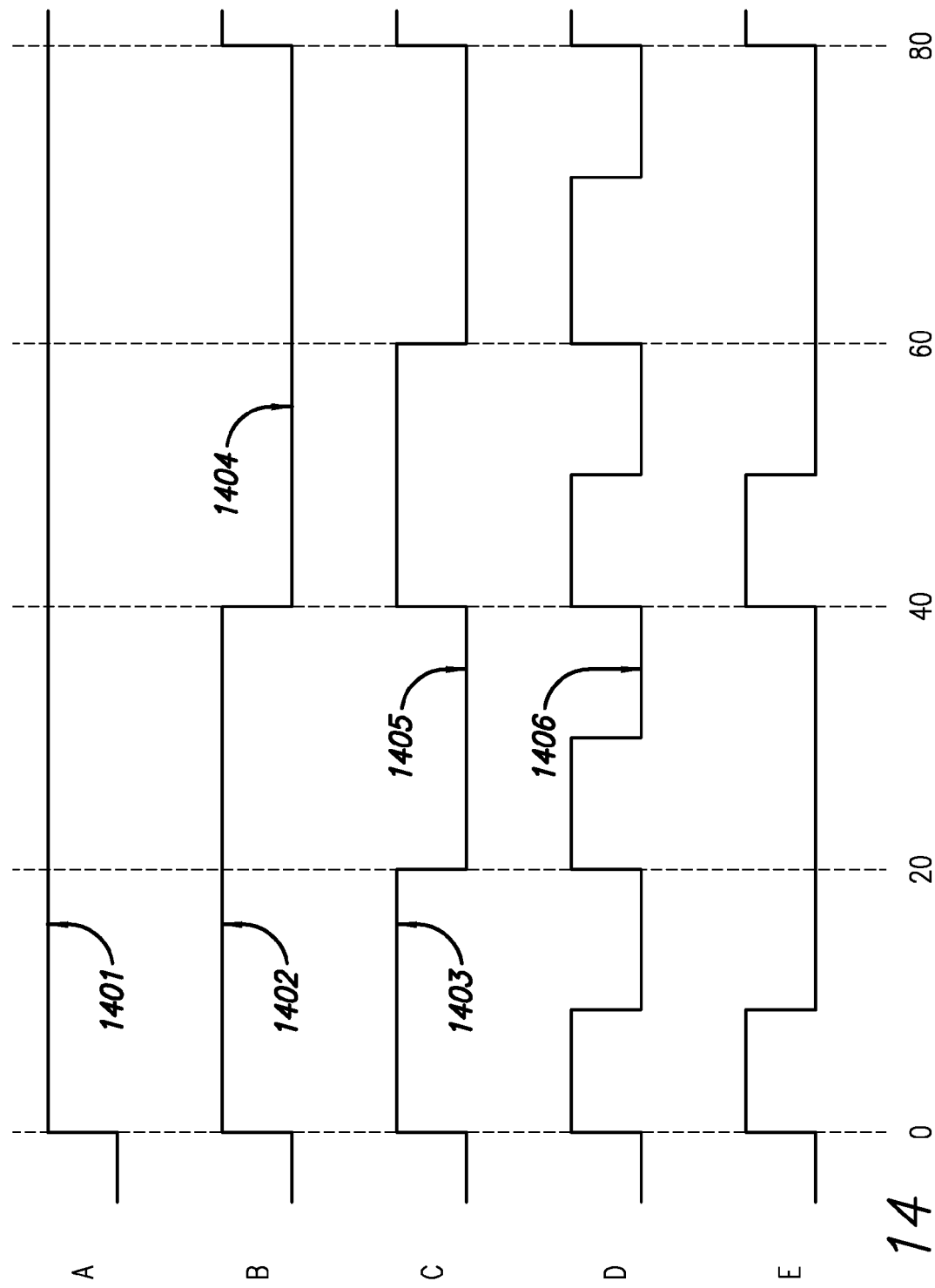
FIG. 14 illustrates different ultrasonic energy pulse characteristics for pulses provided by the power level controller and computer via the handpiece.

A representation of different pulse characteristics for previous operation is presented in FIG. 14. From FIG. 14, operation of pulses may be a constant application of power at a frequency of between about 25 kHz to about 50 kHz as illustrated in Plot A, or once every 80 milliseconds for a duration of 40 milliseconds on and 40 milliseconds off as in Plot B, representing 12.5 pulses per second. Alternately, ultrasonic power delivery may occur once every 40 ms, for 20 ms on and 20 ms off as in Plot C. Plot D shows power applied every 20 ms for 10 ms and turned off for 10 ms. Other non periodic arrangements may be employed, such as shown in Plot E, with application of power for 10 ms periodically every 40 ms, with a resultant 30 ms off time.

These power application intervals represent solid, constant periods when ultrasonic power is being applied to the handpiece and needle at a constant power level for a period of time. Again, while power may appear in the Figures to be applied at a continuous DC type of application, the Figures are intended to indicate actual application of power including a sinusoidal waveform being applied to the piezoelectric crystals at a frequency of generally between about 25 kHz and 50 kHz. The application of power is therefore not truly "constant." Application of power during this 150 ms period is defined as a constant application of a 25 kHz to 50 kHz sinusoid.

Cavitation.

The present design offers enhancements over the waveforms of FIG. 14 by employing beneficial effects of cavitation and applying energy accordingly. Cavitation in the surgical environment may be defined as the violent collapse of minute bubbles in fluid, such as saline, water, or other applicable fluid. Cavitation is the primary means by which cells and nuclei can be broken or cut in ultrasonic surgical systems, including phacoemulsifiers. The system presented above can generate cavitation by providing a series of acoustic pressure waves forming an acoustic pressure field emanating from the tip of the phacoemulsifier handpiece 30. Acoustic pressure waves are the result of the phaco tip oscillating forward and back at the operating frequency, such as at the frequency of approximately 38 kHz.

Cavitation is the generation, oscillation, and collapse of minute bubbles in the operating fluid. In a phacoemulsification or other surgical scenario, bubbles are created by the acoustic waves emanating from the surgical ultrasonic tip, and may therefore be called acoustic cavitation. The violent collapse of these bubbles may create most of the forces that break up nuclei or produce the cutting or chopping characteristics of tissue fragmentation. Other bubble motion under the influence of the pressure field, such as resonant vibration discussed below, may also yield a desirable biological effect.

In this ultrasonic environment, acoustic pressure is proportional to the acoustic source strength Qs or volume velocity of the tip, which is the effective tip area A (typically an annulus) multiplied by tip velocity. Tip velocity is the product of the tip vibration amplitude δ and 2π multiplied by operating frequency. The tip is relatively small in comparison to the acoustic wavelength in fluid and acts as a point radiator of sound or monopole source at the operating frequency.

In this environment, low frequency sound tends to radiate in a spherical manner, with a pressure level that falls inversely with distance from the tip. The pressure field at a distance r from a monopole source pulsating at a frequency ω*(2ρf) is given by:

$$p = \left(\frac{j\rho_0 ck}{4\pi}\right)(Q_s)\frac{e^{-jkr}}{r} \quad (1)$$

where $\rho_o$ and c are the density and sound speed of the medium, k is the wave number, or ω/c, and $Q_s$ is the source strength. Using Equation (1), pressure can be expressed as:

$$p = \frac{j\rho_0 \omega^2 A\delta e^{-jkr}}{4\pi r} \quad (2)$$

From Equation (2), pressure is related to tip area, displacement, and the square of the operating frequency. Equation (2) provides a general guideline for determining pressure equivalence between tips of different sizes, frequencies, and displacements.

Acoustic source strength $Q_s$ may be calculated as follows. Assuming a solid circular, flat end tip, operating at 24,500 Hz, with a radius of 1.44 mm, and a vibration amplitude of 100 μm (tip excursion 200 μm):

$$Q_s = \text{Area} * \text{velocity} \quad (3)$$
$$= (\pi r^2) * \omega * \delta$$
$$= \pi * (.00144)^2 * (2*\pi*24{,}500) * (100*10^{-6})$$
$$Q_s = 100 \times 10^{-6} \text{ meters}^3/\text{second}$$

Total acoustic power in this example, W, may be calculated as follows:

$$W = \rho_0 \times c \times k^2 \times (Q_s)^2 / 8\pi \quad (4)$$
where:
$$k = \omega/c \quad (5)$$
$$= (2*\pi*f)/c$$
$$= 2*\pi*24{,}500/1500 \sim = 100$$
$$W = 1000 * 1500 * 100^2 * (10*10^{-6})^2 / 8\pi$$
$$\sim = 6 \text{ Acoustic Watts}$$

As the sound passes through fluid, such as water, saline, or other liquid, the sound encounters microscopic bubbles. A bubble exposed to the "tensile" or "rarefactional" or "negative" part of the wave has a tendency to expand. A bubble exposed to the "compressional" or "positive" portion of the wave tends to decrease in size or shrink slightly. Gas diffuses into the bubble when in the enlarged state due to force differences. Gas tends to dissipate, or diffuse out, when the bubble decreases in size. Because the surface area of the decreased bubble is less than the surface area of the enlarged bubble, less gas tends to diffuse out during this portion of the cycle than diffused in during the "enlarged" portion of the cycle. Over time the bubble tends to increase in size, a phenomenon known as rectified diffusion. If the pressure variation is not significant, the size difference between the enlarged and shrunken state is not significant enough to provide appreciable net gas inflow.

As bubbles increase in size due to rectified diffusion, these bubbles can attain a size wherein hydrodynamic forces on the bubble, such as gas pressure, surface tension, and so forth, reach dynamic equilibrium or resonance with the applied sound field. In situations of dynamic equilibrium, a bubble can oscillate vigorously, collapse and break apart. This oscillation and collapse of the bubble occurs when the pressure is significant. In the event the pressure is enough to produce rectified diffusion, small bubbles will have a tendency to continuously increase in size, oscillate, and then collapse. Bubbles may also divide without full collapse, resulting smaller bubbles that increase in size and continue the process. This phenomenon may be referred to as stable cavitation.

Stable cavitation produces a collection or cloud of bubbles that tend to operate in a relatively stable manner as long as the pressure field exists. In stable cavitation, many of the bubbles break apart without a full, violent collapse. Inducing stable cavitation may not be well suited to cell and nucleus cutting.

Transient cavitation may be defined as violent bubble collapse. When bubbles violently collapse near a boundary, such as a cell wall, the bubbles expend a significant amount of pressure on the cell wall. The effect is similar to a water hammer producing very high pressures and temperatures concentrated within a small area. These high pressure/high temperature conditions can destroy tissue and denature the proteins in the cell. Transient cavitation results from quick expansion and violent collapse of bubbles of a very specific size relative to the acoustic driving frequency. This quick expansion and violent collapse results from the force of the driving waveform. Transient cavitation is sensitive to the driving waveform pressure level in that transient cavitation may not occur at all below some threshold level. Above the threshold, transient cavitation will result as long as bubbles of the correct size are available.

The absolute threshold for cavitation phenomena is generally frequency dependent. In generating cavitation, the arrangement described herein translates energy from the driving, low frequency ultrasonic waveform into the mechanical manipulation of bubbles. The driving waveform emanating from the phaco tip may be termed a pumping wave. As more cavitation occurs, more energy is received from the pumping wave. At low pressure levels, such as below the threshold for cavitation, the low frequency pressure emitted from the tip is roughly proportional to tip excursion. In this low pressure scenario, little pressure is available to impact the cell wall or nucleus. Some mechanical impact may exist since the phaco tip vibrates and can thus cause frictional heating. An increase in driving excursion level tends to increase cavitation activity. Further drive amplitude increases result in radiated low frequency pressure no longer having the ability to track amplitude. This decorrelation between pressure and amplitude occurs as a result of energy transferring to cavitation. As the drive amplitude is further increased, the low frequency pressure field can decrease. Such a decrease in the pressure field is a result of bubbles obscuring the tip and acting as a cushion shielding the pressure field. This cushion can change the local acoustical properties of the fluid. Thus the ratio of pumping energy to cavitational energy changes as drive amplitude increases.

Figure 15:
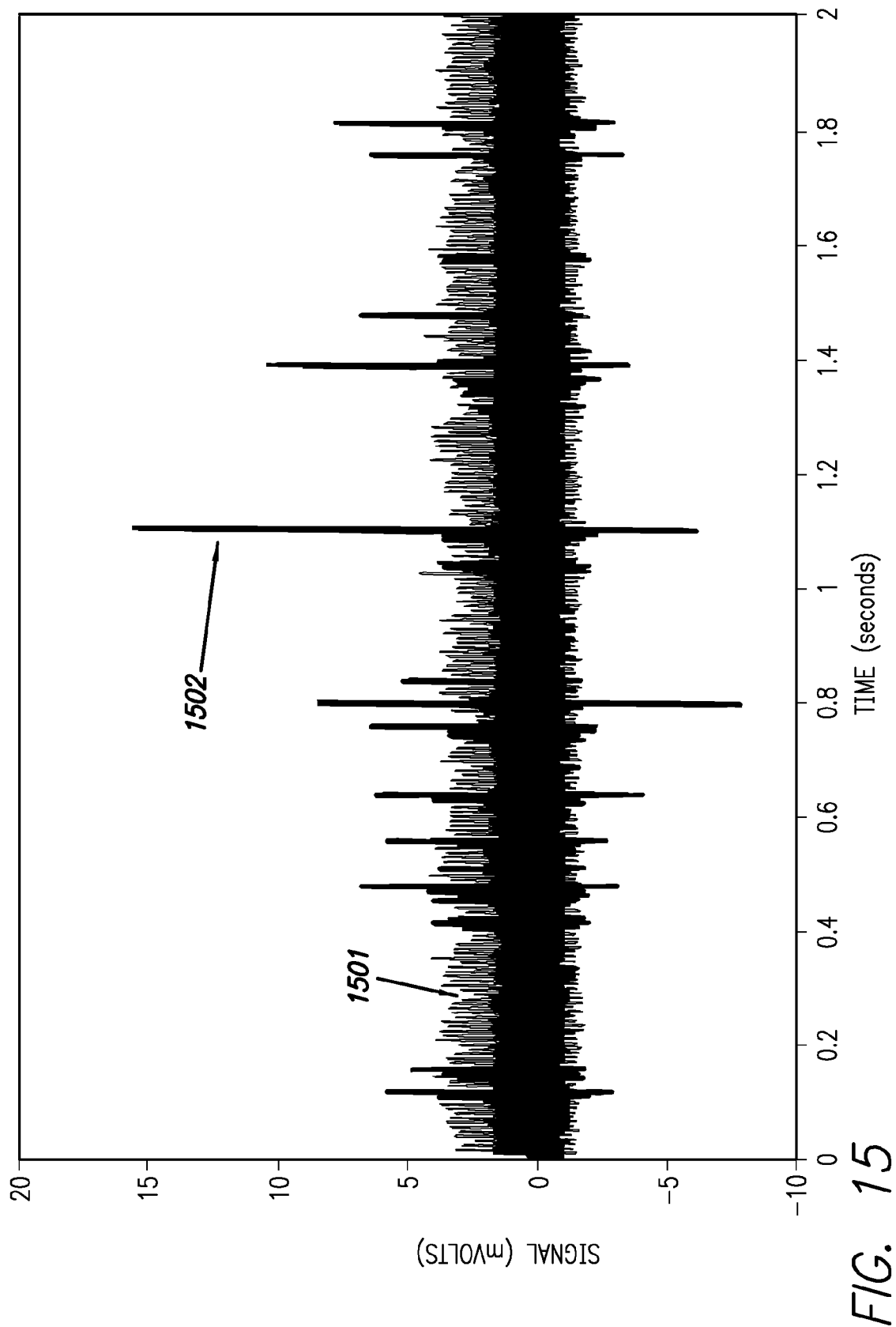
FIG. 15 is a plot of signal strength for a system applying continuous energy in a fluid under different level power settings.

FIG. 15 shows the resultant energy applied to a fluid for a system applying a constant level of energy, i.e. continuous application of power for a period of time, such as 2.0 seconds. The signal 1502 having multiple high amplitude spikes is one having a low power setting, while the signal 1501 exhibiting lower, choppier characteristic has a higher power setting. The low power signal 1502 exhibits relatively large signal excursions, indicative of transient cavitation. Between transient peaks, the signal level for the low power signal 1502 is at approximately the noise floor. The choppier and higher power signal 1501 exhibits a lower peak level, but a continuous signal above the noise floor, indicative of stable cavitation.

Figure 16:
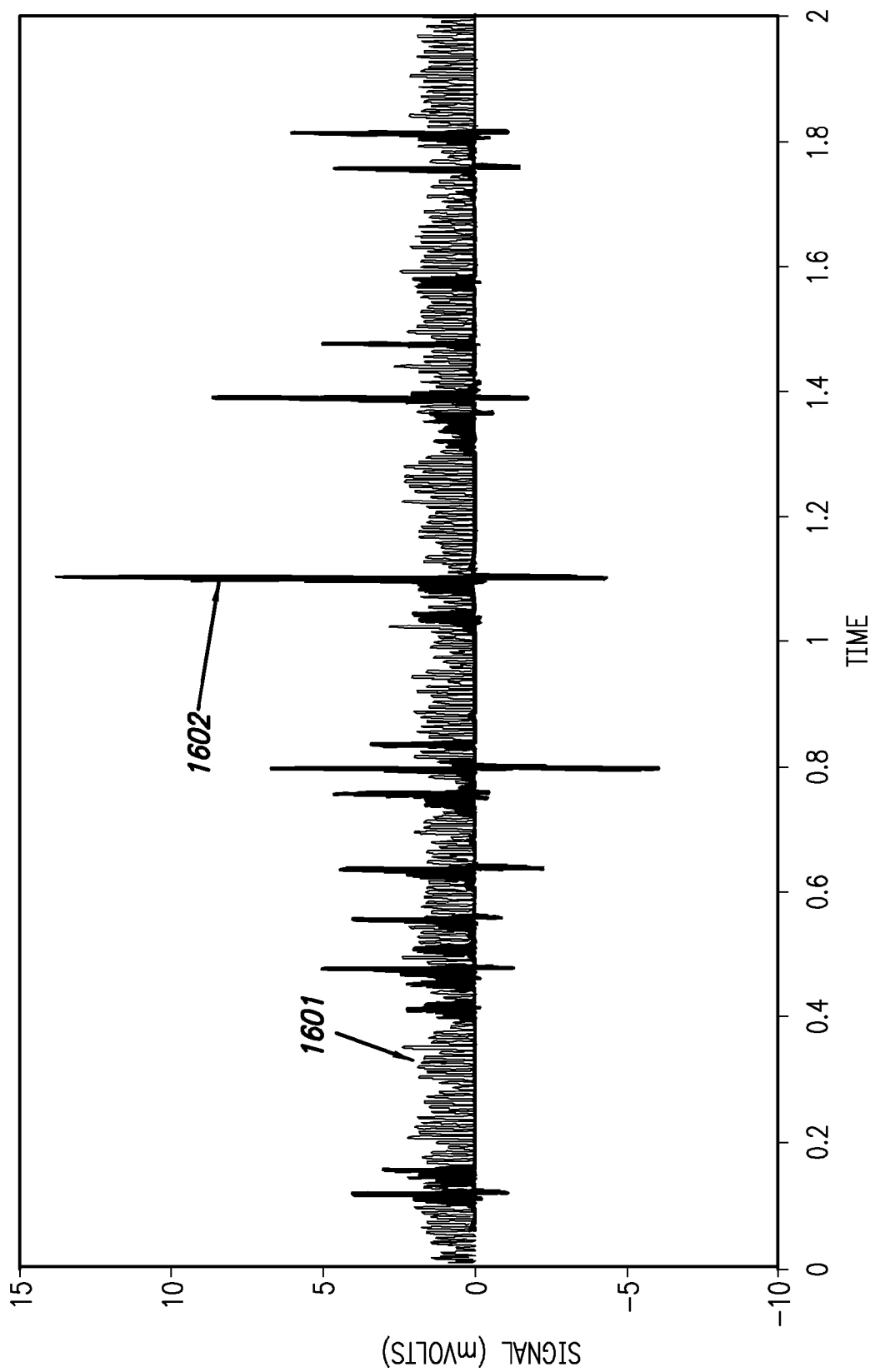
FIG. 16 shows signal strength after noise floor removal and only cavitation excursions plotted for a system applying continuous energy in a fluid under different level power settings.

Removal of the noise floor and plotting of cavitation excursions for the system of FIG. 15 is presented in FIG. 16. The two waveforms, high power signal 1601 and low power signal 1602 display nearly identical overall cavitational energy over the time period shown. Thus while transient cavitation occurs less frequently, transient cavitation tends to release greater energy to the region or environment.

Figure 17:
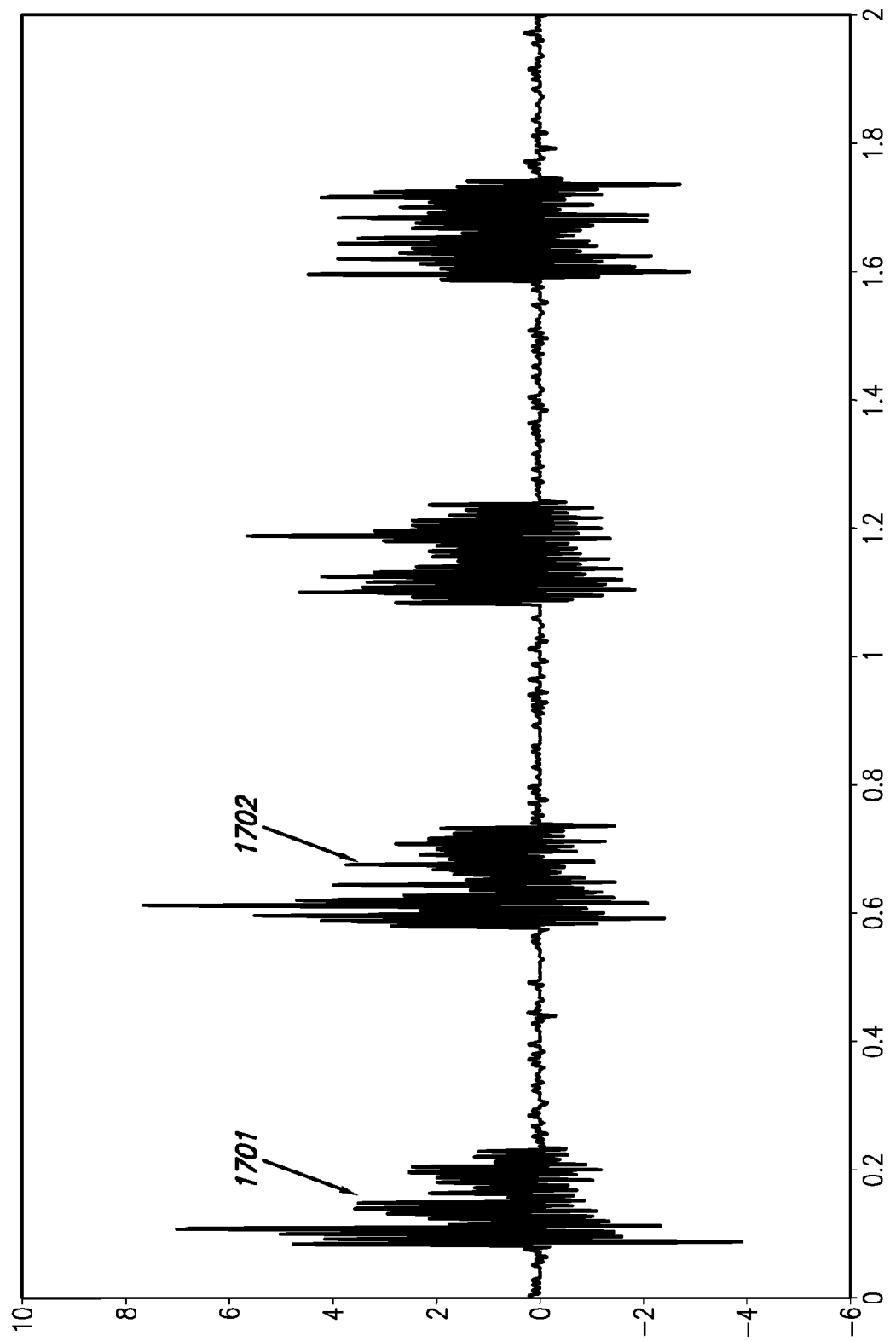
FIG. 17 illustrates performance of a system employing periodic power application settings.
Figure 18:
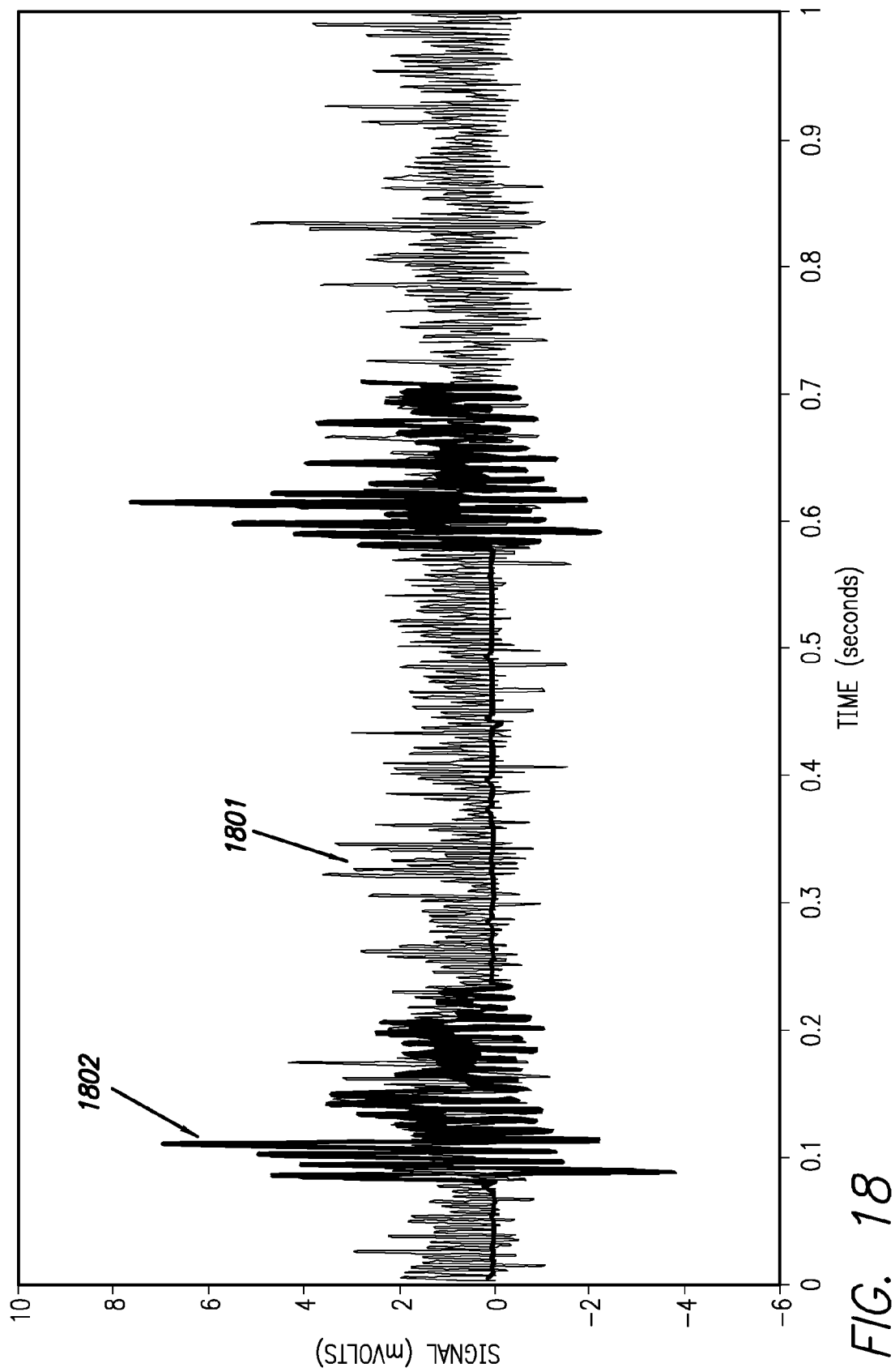
FIG. 18 compares signal strength for continuous operation against periodic power application.

FIG. 17 shows the response of a system wherein power is applied in shorter bursts, such as approximately 0.15 milliseconds on followed by approximately 0.35 milliseconds off. The plot of FIG. 17 illustrates performance after noise thresholding. The first two bursts 1701 and 1702 begin with significant transient cavitation, but this transient cavitation tends to fall off relatively rapidly. FIG. 18 shows this long pulsing, 0.15 milliseconds on followed by 0.35 milliseconds off, as compared to continuous application of power. The long pulsing signal 1802 and the continuous signal 1801 have similar total cavitational energy over the time period, but the pulsed response 1802 uses less than approximately half the drive power. This lower drive power results from the system being energized for less than approximately half the time.

Figure 19:
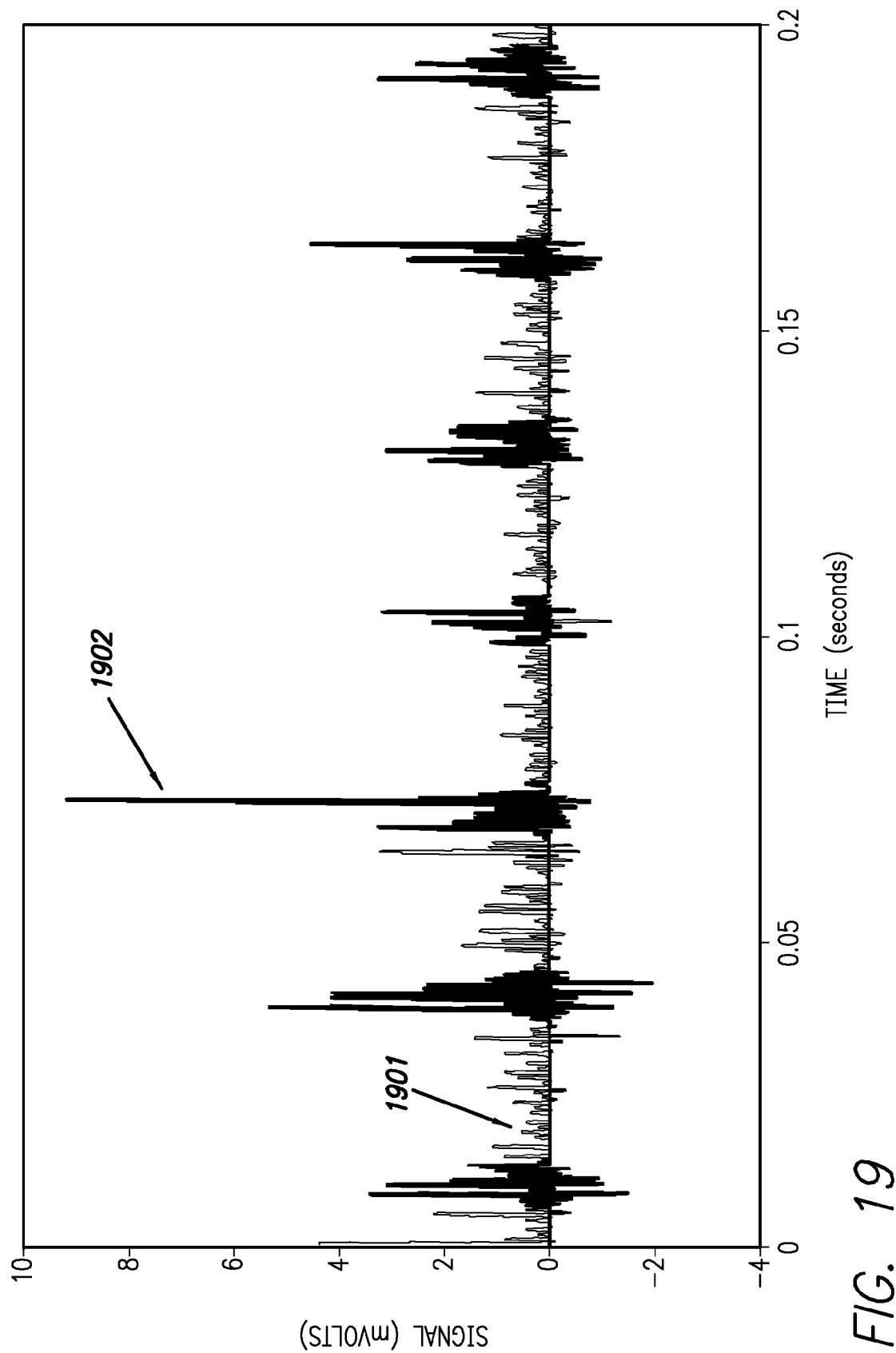
FIG. 19 shows a comparison between continuous operation signal strength and periodic microburst energy application signal strength.

FIG. 19 illustrates application of continuous power 1901 in the environment and a shorter burst arrangement 1902. This shorter burst period 1902 employs a series of bursts such as repeatedly applying energy for 6 ms and resting for 24 ms for a total period of 0.2 seconds, then applying de minimis power, such as zero power, for 0.5 seconds. FIG. 19 illustrates that nearly every burst of drive frequency energy in this shorter burst period 1902 tends to generate transient cavitation. The time between bursts is believed to enable fluid to move sufficiently to replenish the area with bubbles of sufficient size, or dissolved gas, thus producing an environment again receptive to transient cavitation.

Figure 20:
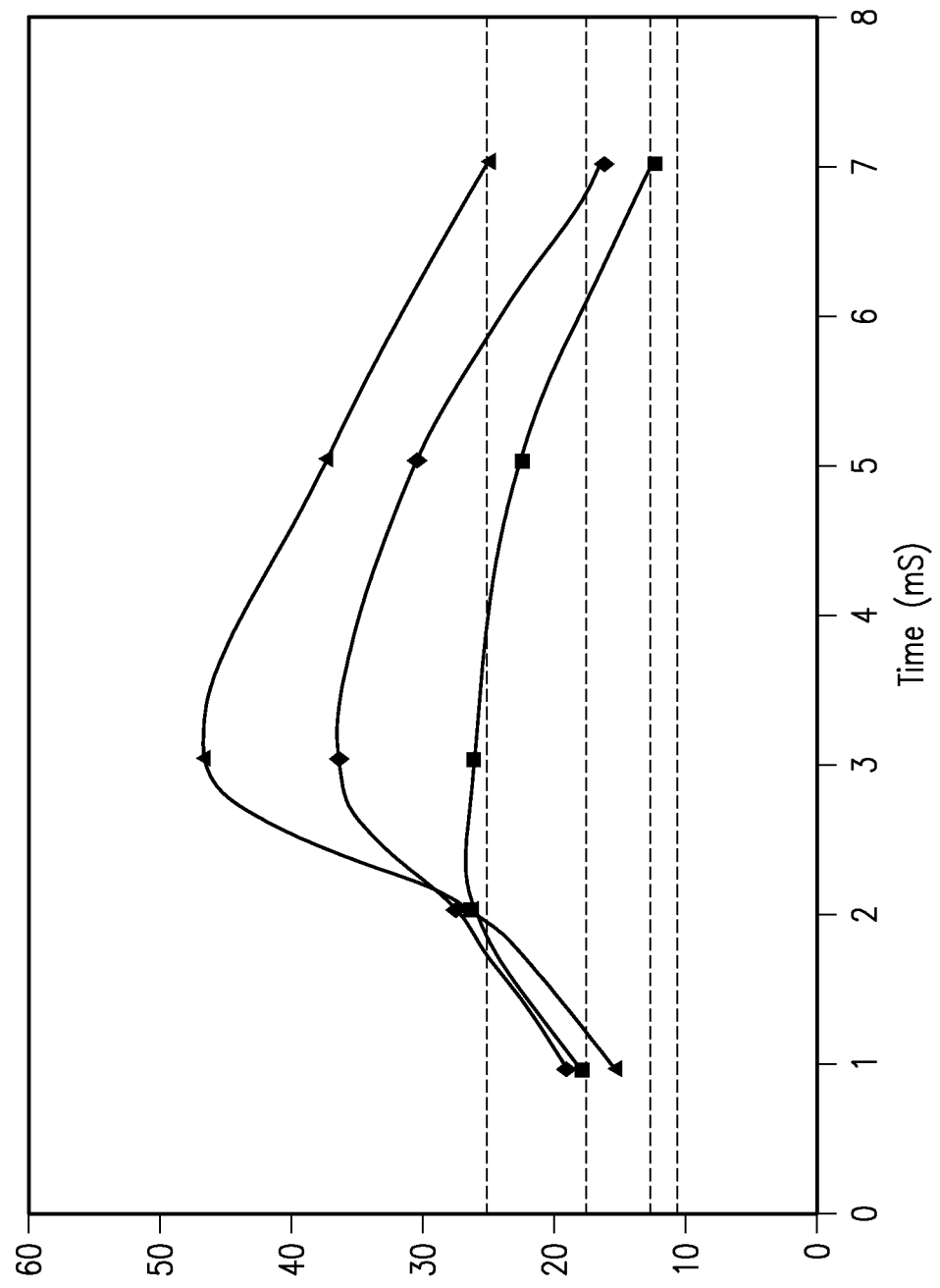
FIG. 20 illustrates relative cavitation energy over time for various energy application settings.

In the present system, based on observation of performance in the presence of short duration energy delivery, cavitation relates to energy delivery as shown in FIG. 20. FIG. 20 represents various energy applications in the phacoemulsification environment and the resultant cavitational energy. From FIG. 20, two to three milliseconds are typically required for the cavitational energy to rise to a maximum. Two to three milliseconds represents the time required for the phaco tip to achieve the full requested excursion and for the cavitation process, specifically transient cavitation, to commence. Once started, energy delivered tends to fall off, representing the transition from transient to stable cavitation. After six milliseconds, the handpiece becomes de-energized, and only residual "ringing" of the tip produces cavitation.

The dashed lines in FIG. 20 represent energy readings taken in the presence of a continuous application of energy, such as shown in FIGS. 15, 16, 18, and 19. From FIG. 20, cavitation energy level is significantly lower in continuous mode.

Modulated Energy Delivery.

Figure 21:
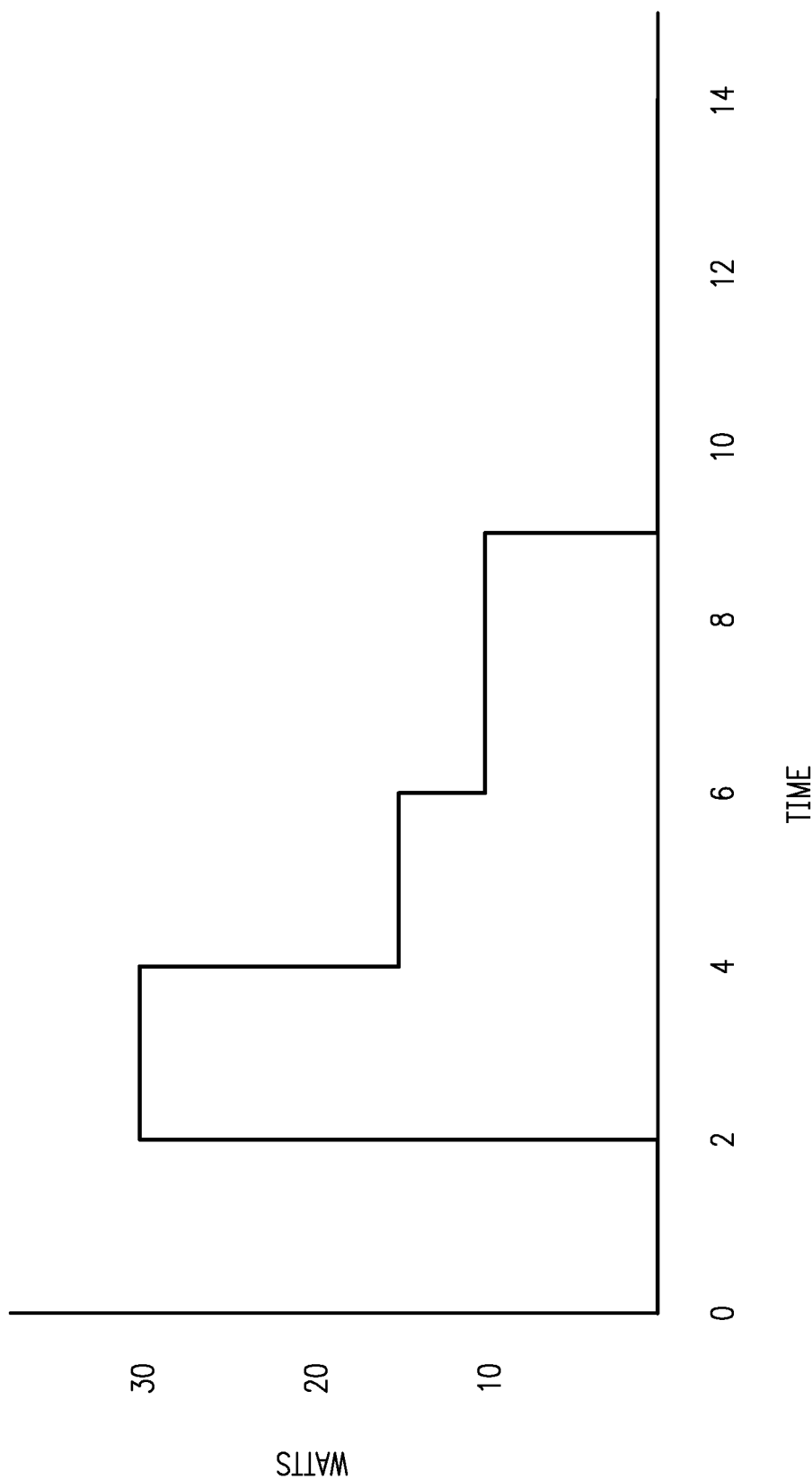
FIG. 21 shows a waveform according to the present design.

The present design employs stable cavitation and transient cavitation as follows. Power is applied in brief pulses, with these brief pulses having divided energy levels for the phaco environment presented above. In particular, a waveform such as that shown in FIG. 21 may be employed. Other similar waveforms may be employed and depend on the environment encountered, including but not limited to phaco conditions, tip size, operating frequency, fluid conditions, and occlusion conditions. FIG. 21 shows a modulated pulse delivering initial power by an initial energy period 2101 at 30 watts for a brief duration, such as 2 ms. The 30 watts represents input to the handpiece. The second period 2102 represents power delivered at 15 watts for a period of 2 ms. The third period 2103 represents a time period, in this example three milliseconds, delivered at a specific level, such as 10 watts. The goal of the modulated or stepped power delivery arrangement is to initiate needle stroke above the distance necessary to generate transient cavitation as rapidly as possible. Once the power threshold required to induce transient cavitation has been achieved, power may be reduced for the remainder of the pulse.

Figure 22A:
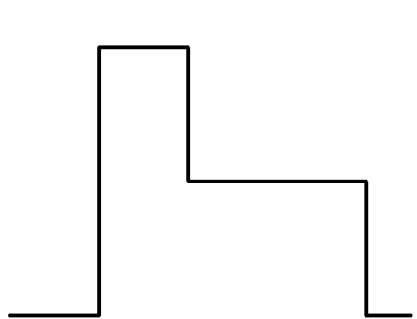
FIGS. 22A through 22I show alternate examples of waveforms according to the present design.
Figure 22B:
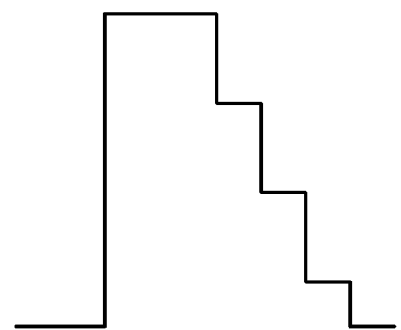
Figure 22C:
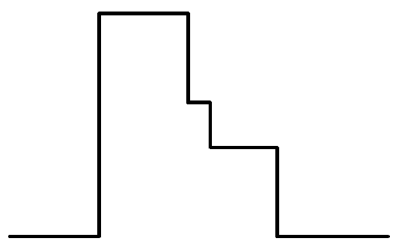
Figure 22D:
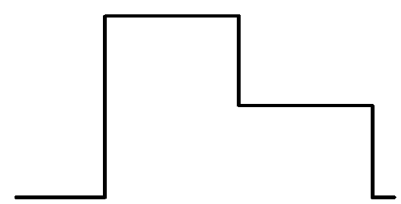
Figure 22E:
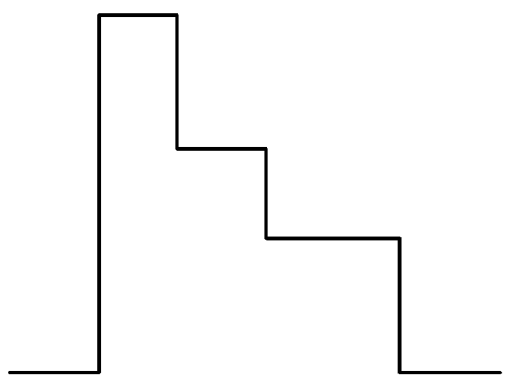
Figure 22F:
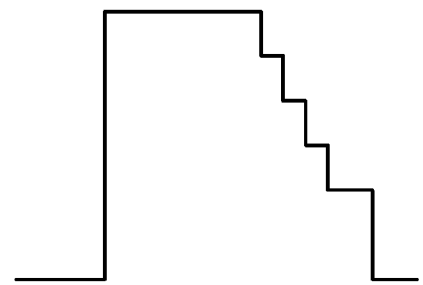

As may be appreciated by those skilled in the art, other timing and power implementations may be employed. Examples of power schemes are provided in FIGS. 22A-F, where power levels and timing are varied. The goal of varying the time and power is to attain transient cavitation as quickly as possible in the environment presented without generating significant heat. FIG. 22A shows a two step modulated pulse at 30 watts for 2 ms and 15 watts for 4 ms. FIG. 22B is a 2.5 ms 35 watt pulse, followed by a 1 ms 25 watt pulse, followed by a 1 ms 15 watt pulse, followed by a 1 ms 5 watt pulse. FIG. 22C shows a 25 watt pulse for 2 ms, a 15 watt pulse for 0.5 ms, and a 10 watt pulse for 2.5 ms. FIG. 22D is a 20 watt pulse for 3 ms and a 10 watt pulse for 3 ms. FIG. 22E shows a 40 watt pulse for 1.8 ms, a 25 ms pulse for 2 ms, and a 15 watt pulse for 3 ms. FIG. 22F is a 30 watt pulse for 3.5 ms, a 25 watt pulse for 0.5 ms, a 20 watt pulse for 0.5 ms, a 15 watt pulse for 0.5 ms, and a 10 watt pulse for 1 ms. As may be appreciated by one of ordinary skill in the art, other times and durations may be employed depending on circumstances.

Figure 22G:
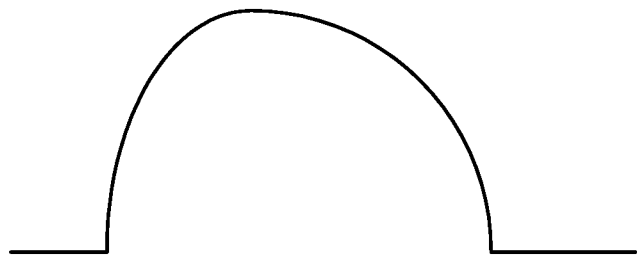
Figure 22H:
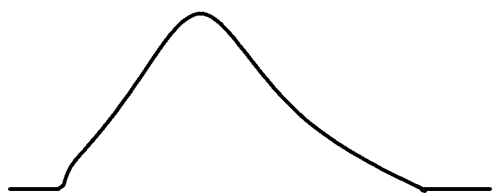
Figure 22I:
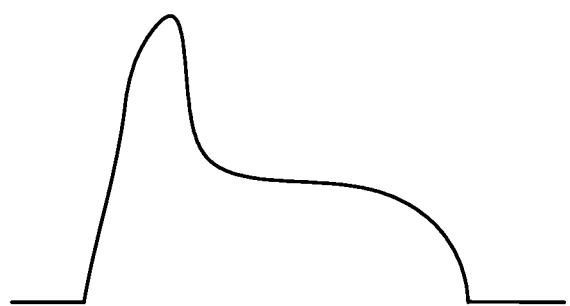

While FIGS. 22A-F show essentially square waves going on and off at specific times, it is not essential that the waves be square in nature. FIGS. 22G-I illustrate an alternative aspect of the invention wherein rounded waves, or graduated power delivery curves, are applied to the surgical area. As shown in FIGS. 22G-I, and as may be appreciated by those skilled in the art, sufficient power is delivered based on the circumstances presented to induce transient cavitation, typically by delivering an initial higher powered surge or burst of energy, followed by a dropoff in energy from the initial surge. The magnitude and time of the initial energy surge depends on circumstances presented, and may exhibit characteristics similar to or based in whole or in part upon curves similar to those shown in FIG. 20 for a typical phacoemulsification surgical environment.

The important factor in the present design is to provide transient cavitation in the environment in a relatively brief amount of time followed by a permissible dropoff in energy in an attempt to minimize energy delivered to the region. Thus a strong or high energy initial pulse followed shortly thereafter or immediately thereafter by at least one lower power pulse is the critical modulated power delivery method to achieve the foregoing desired performance.

In the environment discussed herein, application of ultrasonic energy may be characterized as a strong or high energy short pulse being applied for a short duration followed by a dropoff in ultrasonic energy applied. Such waveforms include but are not limited to those waveforms shown in FIGS. 22A-22I. Cavitational energy, as represented in FIG. 20, is related to the application of power, but may in fact occur for a different time period than the ultrasound energy period. For example, but not by way of limitation, ultrasound energy may be applied for approximately three milliseconds, reaching a peak during these three milliseconds, while the resultant cavitational energy may reach a peak at a later time, such as at six milliseconds. Longer or shorter periods may be employed and/or observed, and the effectiveness of the differing time periods depends on the environment wherein the time periods are employed.

From the foregoing, depending on output conditions, transient or stable cavitation may be generated in different circumstances by the ultrasonic device. This cavitation may be employed in varying environments in addition to those disclosed herein, including but not limited to a diagnostic environment and a chemical processing environment. The cavitation may also be employed in medical treatments or to enhance medical treatments. Enhancement of medical treatments may include, for example, assisting or accelerating the medical treatment. With respect to chemical processing, applying energy in the manner described can have a tendency to minimize heat resulting from ultrasound energy transmission, and can tend to minimize input energy required to effectuate a given chemical result.

Transient cavitation tends to require certain specific conditions to occur effectively in the phaco environment, including but not limited to the availability of properly sized initial bubbles and/or dissolved gas in the fluid. When bubbles of the proper size and/or dissolved gas are not available, either because of low flow or in the presence of a high output level in a continuous power application mode, transient cavitation tends to transition to stable cavitation. Energy present in transient cavitation tends to be higher than that of stable cavitation. Pulsing energy as opposed to constant energy can provide certain advantages, such as enabling the fluid to resupply properly sized bubbles to facilitate transient cavitation, consuming and delivering less total power with less likelihood of causing thermal damage to tissue. Further, cavitation in the presence of a pulsed energy delivery mode, for the phaco system described herein, requires approximately two or three milliseconds to attain a maximum value. Cavitation begins to then decrease as transient cavitation transitions to stable cavitation.

Figure 23:
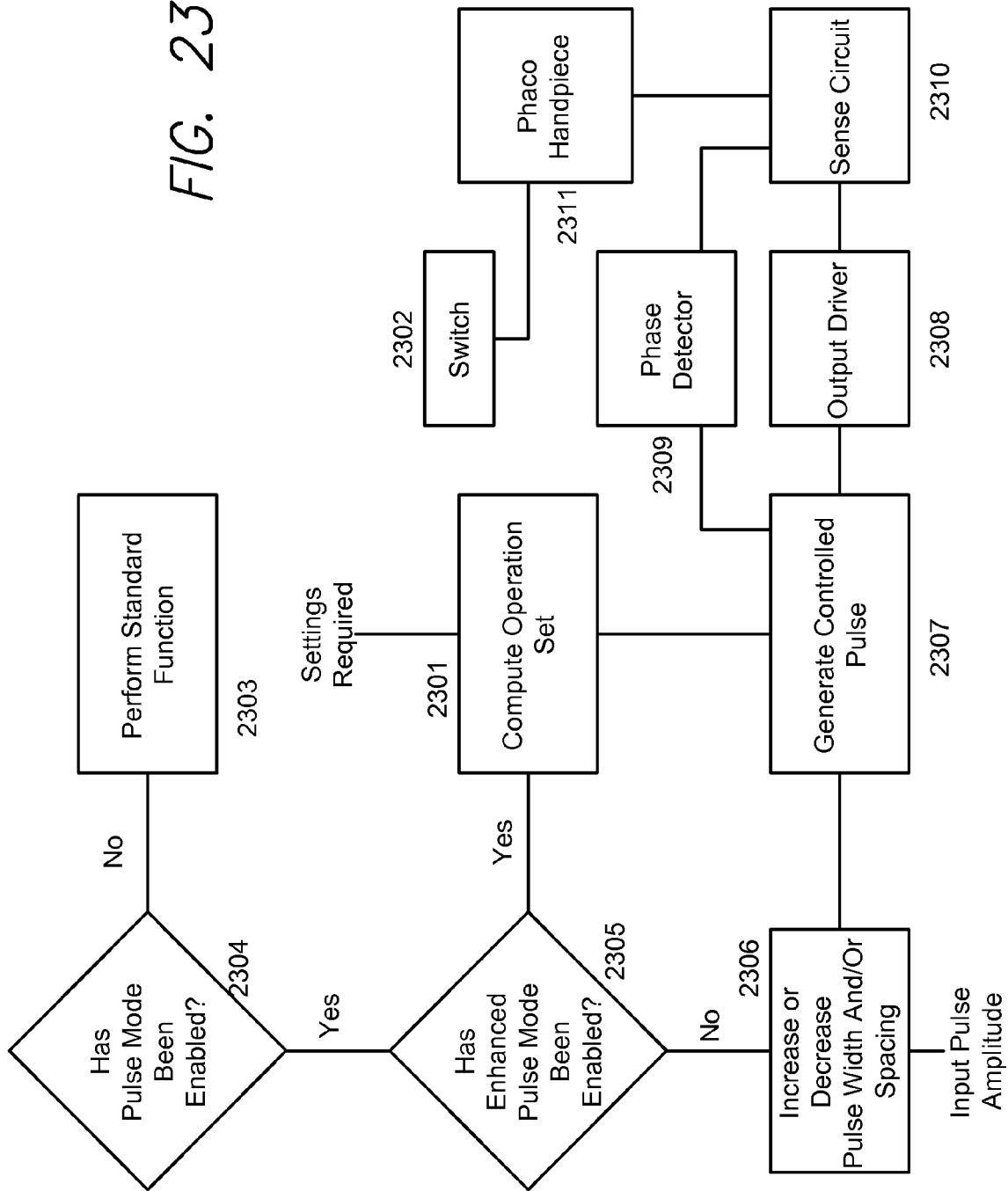
FIG. 23 presents a conceptual block diagram of computation and delivery of the enhanced ultrasonic energy waveform of the present invention.

The pulsing of energy described herein may be performed in software, hardware, firmware, or any combination thereof, or using any device or apparatus known to those skilled in the art when programmed according to the present discussion. A sample block diagram of the operation of the invention as may be implemented in software is presented in FIG. 23, which is an extension of the implementation of FIG. 13. From FIG. 23, after evaluating whether pulse mode has been enabled, the system evaluates whether enhanced pulse mode has been enabled. If not, the system proceeds according to FIG. 13.

If enhanced pulse mode has been enabled, the Settings Required are received. Settings Required may include, but are not limited to, overall cycle time, a desired procedure or function to be performed (sculpting, chopping, etc.), desire to provide bursts or long continuous periods of power application, desired transient cavitation energy application amplitude, desired transient cavitation energy application period, desired lower amplitude energy level, desired lower amplitude energy duration, pause between transient application energy bursts, and/or other pertinent information. Certain lookup tables may be provided in determining Settings Required, including but not limited to tables associating popular settings with the specific performance parameters for the desired setting. For example, if the desired function is "chop," the system may translate the desired "chop" function selection into a standardized or predetermined set of performance parameters, such as a 150 millisecond "burst on" period, followed by an 350 ms "long off period," where the "burst on" period comprises 1 millisecond transient cavitation high energy periods followed by a 3 millisecond lower energy period, followed by a 1 millisecond pause, repeated sufficiently to fill the 150 millisecond "burst on" period. The system takes the Settings Required and translates them into an Operation Set, or operation timing set, the Operation Set indicating the desired operation of the phacoemulsification handpiece tip when performing ultrasonic energy or power delivery.

Input 2302 represents an optional input device, such as a foot pedal, electronic or software switch, switch available on the phacoemulsification handpiece, or other input device known to those skilled in the art, that allows the surgeon/operator to engage and enable ultrasonic power to be applied according to the Operation Set. For example, a foot pedal may be supplied that issues an on/off command, such that when depressed power is to be applied according to the operation set, while when not depressed power is not supplied to the phacoemulsification handpiece tip. Different input devices may enable different modes of operation. For example, a multiple position switch may be provided that allows for application of ultrasonic power according to one Operation Set, while moving the switch to another position allows for application of ultrasonic power according to a different Operation Set. Alternately, one position of the switch may allow for power application at one level according to one Operation Set, while another position of the switch may enable a higher ultrasonic power level at the same or a different operational timing set. Operation Set as used herein refers to the timing of pulses and/or energy applications and on/off periods for the application of power as described herein. Switching may also be nonlinear, such as one detent or setting for the switch providing only irrigation to the handpiece 30, a second detent or setting providing a pump on plus irrigation, and a third detent or setting providing irrigation and aspiration wherein ultrasound is introduced and may be increased by applying further engagement of the switch or foot pedal. In this instance, a foot pedal depressed to the third position or detent will enable the operator or surgeon to apply energy according to a base operational timing set and amplitude, such as a first operational timing set with a first transient cavitation inducing amplitude, while further depression of the foot pedal would allow application of a second operational timing set and/or a second amplitude. If increased amplitude is desired, depressing the foot pedal past the third detent may linearly change the amplitude from a value of 0% of available ultrasonic power or tip stroke length to a value of 100% of ultrasonic power or tip stroke length, or some other value between 0% and 100%. In the present design, amplitudes during energy application periods typically range from about 0 watts to 35 watts at 100% power (input to the handpiece 30).

As may be appreciated, virtually any Operation Set and operation timing set may be employed while within the course and scope of this invention. In particular, the system enables operation in multiple configurations or operational timing sets, each typically accessible to the user via the computer. For example, the user may perform a chop operation using one operational timing set, a sculpt operation using another operational timing set, and when encountering particular special conditions employing yet another operational timing set. These configurations may operate dynamically, or "on the fly."

The system typically has a frame rate, which may be any period of time less than the smallest allowable power on or power off period for the device. A counter counts the number of pulses, and if the Operation Set dictates that ultrasonic power is to be delivered at a certain frame number, an indication in the form of an electronic signal is delivered to the handpiece tip at that frame time. Other implementations beyond that shown in FIG. 23 may be employed while still within the scope of the present invention.

Figure 24A:
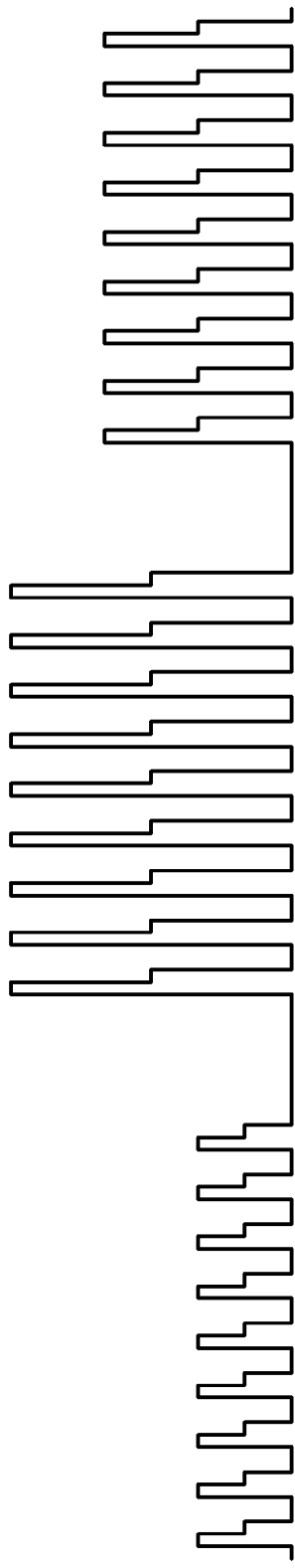
FIGS. 24A and 24B illustrate waveforms provided in the presence of an occlusion or other sensed change in flow, pressure, or vacuum conditions.
Figure 24B:
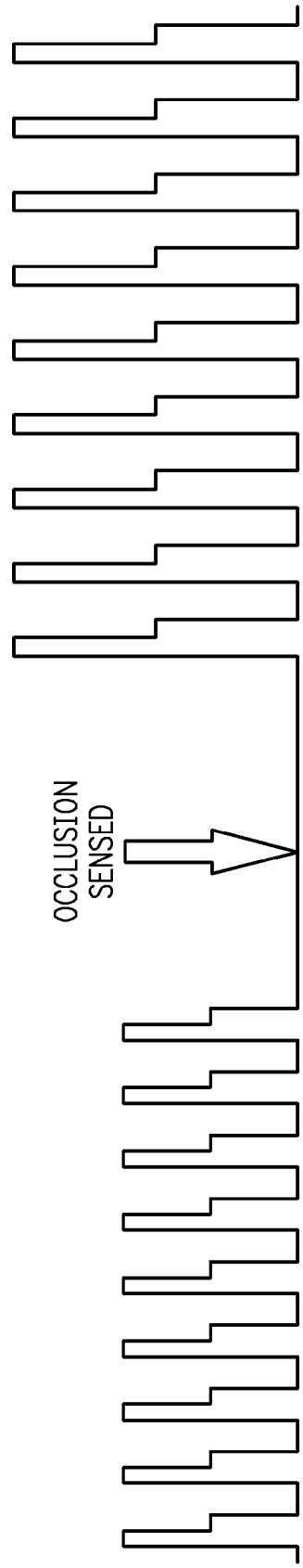

FIG. 24A illustrates the automatic or user controlled altering of the amplitude, with three different amplitude levels having the same timing. Alternate timing may be made available in addition to the different amplitudes. Additionally, the system may operate to address receipt or encounter of an occlusion as sensed by a sensor, typically located in the system. As in FIGS. 3 and 4, the handpiece or system may employ a sensor to sense a change in flow or vacuum, i.e. pressure, conditions. A change in flow or vacuum/pressure conditions sensed by the sensor indicates the presence of an occlusion, and upon sensing the presence of an occlusion, the handpiece or system may feed back an occlusion indication to the computer 18. An occlusion indication may cause the computer 18 to automatically alter the Operation Set to an occlusion related Operation Set such as that illustrated in FIG. 24B.

It will be appreciated to those of skill in the art that the present design may be applied to other systems that perform tissue extraction, such as other surgical procedures used to remove hard nodules, and is not restricted to ocular or phacoemulsification procedures. In particular, it will be appreciated that any type of hard tissue removal, sculpting, or reshaping may be addressed by the application of ultrasonic power in the enhanced manner described herein.

Although there has been hereinabove described a method and apparatus for controlling the ultrasonic power transmitted from a phacoemulsification handpiece utilizing, inter alia, the voltage current phase relationship of the piezoelectric phacoemulsification handpiece and delivering ultrasonic power using relatively short pulses comprising multiple brief power bursts sufficient to induce transient cavitation in the environment presented, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for delivering energy during a surgical procedure, comprising:
  applying energy to an ocular region of a patient during a modulated energy delivery period, comprising:
    applying energy during a plurality of burst periods, said burst periods comprising an initial energy burst period having duration less than 3.5 milliseconds during which energy is applied at a first predetermined nonzero level followed a predetermined time thereafter by a nonzero subsequent energy burst period during which energy is applied at a second predetermined nonzero level lower than the first predetermined nonzero level.

2. The method of claim 1, wherein the predetermined time is zero.

3. The method of claim 1, wherein said burst periods further comprise a second nonzero subsequent energy burst period.

4. The method of claim 3, wherein:
  said nonzero subsequent energy burst period comprises a first amplitude; and
  said second nonzero subsequent energy burst period comprises a second amplitude;
  and said first and second amplitude are different.

5. The method of claim 3, wherein:
  said nonzero subsequent energy burst period comprises a first amplitude; and
  said second nonzero subsequent energy burst period comprises a second amplitude;
  and said first and second amplitude are equal.

6. The method of claim 1, wherein the surgical procedure is performed in a surgical environment, and wherein applying energy during the burst periods comprising an initial energy burst period followed a predetermined time thereafter by the nonzero subsequent energy burst period tends to induce transient cavitation in the surgical environment.

7. The method of claim 1, wherein the initial energy burst induces transient cavitation.

8. The method of claim 1, wherein initial energy burst duration is more than 1.8 milliseconds and induces transient cavitation.

\* \* \* \* \*